United States Patent [19]

Blaiseu et al.

[11] Patent Number: 5,446,138

[45] Date of Patent: Aug. 29, 1995

[54] RECOMBINANT DNA CODING FOR A PROTEIN WITH ENDOCHITINASE ACTIVITY

[75] Inventors: Pierre-Louis Blaiseu, Villejuif; Richard Legoux, Le Faget; Jean-Jacques Leguay, Paris; Michel Schneider, Toulouse, all of France

[73] Assignees: Elf Sanofi, Paris; Societe Nationale Elf Aquitaine, Courbevoie, both of France

[21] Appl. No.: 939,501

[22] Filed: Sep. 8, 1992

[30] Foreign Application Priority Data

Sep. 6, 1991 [FR] France ................. 91 11072

[51] Int. Cl.$^6$ .............. C07H 21/04; C12N 5/14; C12N 1/15; C12N 1/19; C12N 1/21
[52] U.S. Cl. ................... 536/23.74; 536/23.2; 435/240.4; 435/252.3; 435/254.2; 435/254.11
[58] Field of Search ....... 800/205, DIG. 17, DIG. 43, 800/DIG. 40; 536/27, 23.74, 23.2; 935/66, 67, 68, 69, 73; 435/41, 69.1, 70.1, 71.1, 172.1, 172.3, 240.4, 240.49, 240.5, 240.51, 252.3, 254.2, 243, 254.11

[56] References Cited

U.S. PATENT DOCUMENTS 4,394,443  7/1983  Weissman et al. ................. 435/6

FOREIGN PATENT DOCUMENTS 290123   11/1988  European Pat. Off. .
437320    7/1991  European Pat. Off. .
88/00976  2/1988  WIPO .
90/07001  6/1990  WIPO .

OTHER PUBLICATIONS

Jones et al (1988) Mol Gen Genet. 212: 536–542.
Rothstein et al (1984) Nature 308: 662–665.
Vasseur et al. (1990) J. Gen Microbiol 136: 2561–2567.
Malardier et al (1989) Gene 78: 147–156.
Comai et al (1988) J. Biol Chem 263(29): 15104–15109.
A. Srivastava et al., "Secretion of Chitinase by Aphanocladium album, a Hyperparasite of Wheat Rust", Experientia, vol. 41, 1985, pp. 1612–1613.

*Primary Examiner*—David T. Fox
*Assistant Examiner*—E. F. McElwain
*Attorney, Agent, or Firm*—Foley & Lardner

[57] ABSTRACT

Recombinant DNA which codes for a protein with endochitinase activity or for a precursor thereof, comprising the sequence (a1) (SEQ ID NO. 1).

17 Claims, 12 Drawing Sheets

FIG. 1A

```
  1  AGCAACTCAATAGGTACAAGCCTAACAGCATAGCTCCCTCTAGAGTCAGCACGCCGAATC                                          60

61  AGTTGATTCTCTACAACCTTCTGTACCTCAACTACTATGTTGAGCTTTGTCAAAAAGTCG                                         120
                                        MetLeuSerPheValLysSer
              PstI
121  ATCGCCTTGGGTGGGCGGCCCTGCAGGCGGTCACTGCCCTGGCCACTGCCCAATCTCCAGTGAA                                   180
     IleAlaLeuValAlaAlaAlaLeuGlnAlaAlaThrAlaLeuAlaThrAlaProIleSerSerGlu
                                           AccI
181  GCTGGGTGTTGAGAAGCGGTAGTGGTTTTGCAAATGCCGTCTACTTCACCAACTGGGGC                                        240
     AlaGlyValGluLysArgSerGlySerGlyPheAlaAsnAlaValTyrPheThrAsnTrpGly

241  ATTTATGGCCGCAACTTCCAGCCCTGCCGACCTTCCTGCCGGAGATTACTCACGTACTC                                        300
     IleTyrGlyArgAsnPheGlnProAlaAspLeuProAlaSerGluIleThrHisValLeu

301  TACTCCTTCATGAATGTCCGCGCAGATGGCACCATCTTTTCCGGTGATACCTATGCCGAC                                       360
     TyrSerPheMetAsnValArgAlaAspGlyThrIlePheSerGlyAspThrTyrAlaAsp

361  TACGAGAAGCACTACGCTGGTGACTCTTGGAACGATGTGGGCACGAACGCTTACGGTTGT                                       420
     TyrGluLysHisTyrAlaGlyAspSerTrpAsnAspValGlyThrAsnAlaTyrGlyCys

421  GTTAAGCAACTTTATCTTCTCAAGAAGCAGAACCGCAACATGAAGGTGATGCTGTCGATT                                       480
     ValLysGlnLeuTyrLeuLeuLysLysGlnAsnArgAsnMetLysValMetLeuSerIle
```

```
                    AccI
481  GGTGGTTGGACATGGTCTACCAACTTCCCCGCTGCCGCCAGCTCGGCTGCTACCCGAAAG   540
     GlyGlyGlyTrpTyrThrThrTrpSerThrAsnPheProAlaAlaSerSerAlaAlaThrArgLys
541  ACTTTGCTCTCAGTCTGCTGTTGGCTTCATGAAGGACTGGGGTTTCGACGGTATTGATATC   600
     ThrPheAlaGlnSerAlaValGlyPheMetLysAspTrpGlyPheAspGlyIleAspIle
601  GACTGGGAGTACCCCGCCGATGCCACTCAGGCTCAGAATATGGTTCTCTTGCTACAGGCT   660
     AspTrpGluTyrProAlaAspAlaThrGlnAlaGlnAsnMetValLeuLeuLeuGlnAla
661  GTCCGCAGTGAGCTCGACTCCTACGCTGCCCAGTACGCCAAGGGTCACCACTTCCTGCTT   720
     ValArgSerGluLeuAspSerTyrAlaAlaGlnTyrAlaLysGlyHisHisPheLeuLeu
721  TCAATTGCCGCCCCTGCTGGACAATTATAAACAAGCTGAAGTTTGCTGAGCTTGGC      780
     SerIleAlaAlaProAlaGlyProAspAsnTyrAsnLysLeuLysPheAlaGluLeuGly
781  AAGGTTCTCGATTACATTAACCTCATGGCTTACGATTACGATTCTTGGAGCAACTAC     840
     LysValLeuAspTyrIleAsnLeuMetAlaTyrAspTyrAlaGlySerTrpSerAsnTyr
841  ACTGGCCACGATGCCAACATATACGCAAACCCGAGAACCCCAACGCCACCCCTTACAAC   900
     ThrGlyHisAspAlaAsnIleTyrAlaAsnProGlnAlaAsnProAsnAlaThrProTyrAsn
```

FIG. 1C

```
FROM FIG.1B                                                                    FROM FIG.1B

901   ACGGACGATGCTGTCCAGGCCTATATCAACGGCGGCGTCCCTGCCAACAAGATCGTCCTT              960
       ThrAspAspAlaValGlnAlaTyrIleAsnGlyGlyValProAlaAsnLysIleValLeu

961   GGTATGCCAATCTACGGCCGATCCTTCCAGCAAACCGAGGGTATCGGTAAGCCTTACAAT             1020
       GlyMetProIleTyrGlyArgSerPheGlnGlnThrGluGlyIleGlyLysProTyrAsn

1021   GGTATTGGCTCTCTGGTAGCTGGGAGAAACGGTATCTGGGACTACAAGGCTCTCCCAAGGCT           1080
       GlyIleGlySerGlySerTrpGluAsnGlyIleTrpAspTyrLysAlaLeuProLysAla

1081   GGTGCCACCGTCAAGTGCGACGATGCCGACTACAGTCTACAGTCCAAGCACT                     1140
       GlyAlaThrValLysCysAspAspThrAlaLysGlyCysTyrSerTyrAspProSerThr

1141   AAGGAGCTTATTTCTTTCGATACGCCGGCTATGATCAGCACCAAAGTTAGCTGGCTCAAG             1200
       LysGluLeuIleSerPheAspThrProAlaMetIleSerThrLysValSerTrpLeuLys

1201   GGCAAGGGCCCTTGGCGGCAGCATGTTCTGGGAGGCTTCTGCCGACAAGAAGGGCTCGGAC            1260
       GlyLysGlyLeuGlyLeuSerMetPheTrpGluAlaSerAlaAspLysLysGlySerAsp

1261   TCTCTTATTAGCACCAGCCACCAAGGTCTCGGTAGCCAGGACAGCACTCAGAACTACCTC            1320
       SerLeuIleSerThrSerHisGlnGlyLeuGlySerGlnAspSerThrGlnAsnTyrLeu

1321   GACTACCCCTAACTCCAAGTACGACAACATCAAGAAGGGCATGAACTAAGCAGTCGGTGTT           1380
       AspTyrProAsnSerLysTyrAspAsnIleLysLysGlyMetAsn
                                                  |XhoI
1381   TGCATAGCTTGATTGAATGCTCGAGG                                              1405
```

FIG. 2A

```
1    TCGGCCCTCTCTCAACTCTCTTCTCTATCAGCAGCAACTCAATAGGTACAAGCCTAACAGCAT              60

61   AGCTCCCTCTAGAGTCAGCACGCCCGAATCAGTTGATTCTCTACAACCTTCTGTACCTCAA              120

121  CTACTATGTTGAGCTTTGTCAAAAAGTCGATCGCCCTTGGTGGCCCTGCAGGCGGTCA                180
        MetLeuSerPheValLysSerIleAlaLeuValAlaAlaLeuGlnAlaValT

181  CTGCCCCTGGCCACGCCAATCTCCAGTGAAGCTGGTGTTGAGAAGCGCGGTAGTGGTTTTG             240
     hrAlaLeuAlaThrProIleSerSerGluAlaGlyValGluLysArgGlySerGlyPheA

241  CAAATGCCGTCTACTTCACCAACTGGTTTGTGCATCCTCATCTTGTTATCTCTTGTTCGT             300
     laAsnAlaValTyrPheThrAsnTrp

301  AATAGTTAACGAATGTTTAGGGCATTTATGCCGCAACTTCCAGCCTGCCGACCTTCCT               360
                              pGlyIleTyrGlyArgAsnPheGlnProAlaAspLeuPro

361  GCCTCGGAGATTACTCACGTACTCCTTCATGAATGTCCGGCAGATGCCACCATG                   420
     AlaSerGluIleThrHisValLeuTyrSerPheMetAsnValArgAlaAspGlyThrIl

421  TGAGTGATGGAGTTCCTAGATCTTGTGCCGCATTTTCTGACAAAGCAACTAGCTTTCCG              480
                                                        ePheSerG
```

```
481  GTGATACCTATGCCGACTACGAGAAGCACTACGCTGGTGACTGTGAGAATCTCTACATTT   540
     lyAspThrTyrAlaAspTyrGluLysHisTyrAlaGlyAspS

541  CTTTTGGCAAAAGAAGAAACTAACAATTAGCTTGGAACGATGTGGGCACGAACGCTTAC   600
                                                erTrpAsnAspValGlyThrAsnAlaTyr

601  GGTTGTGTTAAGCAACTTTATCTCTCAAGAAGCAGAACCGCAACATGAAGGTGATGCTG   660
     GlyCysValLysGlnLeuTyrLeuLeuLysGlnAsnArgAsnMetLysValMetLeu

661  TCGATTGGTGGTTGGACATGGTCTACCAACTTCCCCGCTGCCCAGCTCGGCTGCTACC   720
     SerIleGlyGlyTrpThrTrpSerThrAsnPheProAlaAlaAlaSerSerAlaAlaThr

721  CGAAAGACTTTTGCTCAGTCTGTGTTGGCTTCATGAAGGACTGGGTTTCGACGGTATT   780
     ArgLysThrPheAlaGlnSerAlaValGlyPheMetLysAspTrpGlyPheAspGlyIle

781  GATATCGACTGGGAGTACCCCGGCCGATGCCCACTCAGGCTCCAGAATATGGTTCTCTTGCTA   840
     AspIleAspTrpGluTyrProAlaAspAlaThrGlnAlaGlnAsnMetValLeuLeuLeu

841  CAGGCTGTCCGCAGTGAGCTCGACTCCTACGCTGCCCAGTACGCGCAAGGGTCACCACTTC   900
     GlnAlaValArgSerGluLeuAspSerTyrAlaAlaGlnTyrAlaLysGlyHisHisPhe

901  CTGCTTTCAATTGCCGCCCCTGCTGGACCTGACAATTATAACAAGCTGAAGTTTGCTGAG   960
     LeuLeuSerIleAlaAlaProAlaProAspAsnTyrAsnLysLeuLysPheAlaGlu
```

FIG. 2C

```
961   CTTGGCAAGGTTCTCGATTACATTAACCTCATGGCTTACGATTACGATTACGCTGGATCTTGGAGC  1020
      LeuGlyLysValLeuAspTyrIleAsnLeuMetAlaTyrAspTyrAlaGlySerTrpSer

1021  AACTACACTGGCCACGATGCCAACATATACGCAAACCCGCAGAACCCAACGCCACCCT         1080
      AsnTyrThrGlyHisAspAlaAsnIleTyrAlaAsnProGlnAsnProAsnAlaThrPro

1081  TACAACACGGACGATGCTGTCCAGGCCCTATATCAACGGGCGGTCCCTGCCAACAAGATC       1140
      TyrAsnThrAspAspAlaValGlnAlaLeuTyrIleAsnGlyGlyValProAlaAsnLysIle

1141  GTCCCTTGGTATGCCAATCTACGGCCGATCCTTCCAGCAAACCGAGGGTATCGGTAAGCCT      1200
      ValLeuGlyMetProIleTyrGlyArgSerPheGlnGlnThrGluGlyIleGlyLysPro

1201  TACAATGGTATTGGCTCTGGTAGCTGGGAGAACGGTATCTGGGACTACAAGGCTCTCCCC       1260
      TyrAsnGlyIleGlySerGlySerTrpGluAsnGlyIleTrpAspTyrLysAlaLeuPro

1261  AAGGCTGGTGCCACCGTCAAGTGCGACGATACCGCCAAGGGATGCTACAGCTACGATCCA       1320
      LysAlaGlyAlaThrValLysCysAspAspThrAlaLysGlyCysTyrSerTyrAspPro

1321  AGCACTAAGGAGCTTATTCTTTTCGATACGCCGGCTATGATCAGCACCAAAGTTAGCTGG       1380
      SerThrLysGluLeuIleLeuPheAspThrProAlaMetIleSerThrLysValSerTrp

1381  CTCAAGGGCAAGGGCCTTGGCGGCAGCATGTTCTGGGAGGCTTCTGCCGACAAGAAGGGC       1440
      LeuLysGlyLysGlyLeuGlyGlySerMetPheTrpGluAlaSerAlaAspLysLysGly
```

FIG. 2D

```
FROM FIG.2C                                                              FROM FIG.2C

1441  TCGGACTCTCTTATTAGCACCAGCCACCAAGGTCTCGGTAGCCAGGACCAGCACTCAGAAC   1500
      SerAspSerLeuIleSerThrSerHisGlnGlyLeuGlyLysGlnAspSerThrGlnAsn

1501  TACCTCGACTACCCTAACTCCAAGTACGACAACATCAAGAAGGGCATGAACTAAGCAGTC    1560
      TyrLeuAspTyrProAsnSerLysTyrAspAsnIleLysLysGlyMetAsn

1561  GGTGTTTGCATAGCTTGATTGATGCTCGAGGTTGGATGTGGTCCGCGCTGTATATATTTC    1620

1621  CAAACCAGCCCTTACCCTGAGGCTTATCAAGTCATTCTATACTTTCAACGTACATATTATT   1680

1681  GCTGCCATTGGCATGCAAATA                                           1701
```

FIG. 3

GlySerGlyPheAlaAsnAlaValTyrPheThrAsnTrpGlyIleTyr
GlyArgAsnPheGlnProAlaAspLeuProAlaSerGluIleThrHis
ValLeuTyrSerPheMetAsnValArgAlaAspGlyThrIlePheSer
GlyAspThrTyrAlaAspTyrGluLysHisTyrAlaGlyAspSerTrp
AsnAspValGlyThrAsnAlaTyrGlyCysValLysGlnLeuTyrLeu
LeuLysLysGlnAsnArgAsnMetLysValMetLeuSerIleGlyGly
TrpThrTrpSerThrAsnPheProAlaAlaAlaSerSerAlaAlaThr
ArgLysThrPheAlaGlnSerAlaValGlyPheMetLysAspTrpGly
PheAspGlyIleAspIleAspTrpGluTyrProAlaAspAlaThrGln
AlaGlnAsnMetValLeuLeuLeuGlnAlaValArgSerGluLeuAsp
SerTyrAlaAlaGlnTyrAlaLysGlyHisHisPheLeuLeuSerIle
AlaAlaProAlaGlyProAspAsnTyrAsnLysLeuLysPheAlaGlu
LeuGlyLysValLeuAspTyrIleAsnLeuMetAlaTyrAspTyrAla
GlySerTrpSerAsnTyrThrGlyHisAspAlaAsnIleTyrAlaAsn
ProGlnAsnProAsnAlaThrProTyrAsnThrAspAspAlaValGln
AlaTyrIleAsnGlyGlyValProAlaAsnLysIleValLeuGlyMet
ProIleTyrGlyArgSerPheGlnGlnThrGluGlyIleGlyLysPro
TyrAsnGlyIleGlySerGlySerTrpGluAsnGlyIleTrpAspTyr
LysAlaLeuProLysAlaGlyAlaThrValLysCysAspAspThrAla
LysGlyCysTyrSerTyrAspProSerThrLysGluLeuIleSerPhe
AspThrProAlaMetIleSerThrLysValSerTrpLeuLysGlyLys
GlyLeuGlyGlySerMetPheTrpGluAlaSerAlaAspLysLysGly
SerAspSerLeuIleSerThrSerHisGlnGlyLeuGlySerGlnAsp
SerThrGlnAsnTyrLeuAspTyrProAsnSerLysTyrAspAsnIle
LysLysGlyMetAsn

FIG. 4A

```
  1  GGATCCGCTAACTGACATCGATATACACAATGTTGAGCTTTGTCAAAAAGTCGATCGCCT   60
 61  TGGTGGCGGCCCCTGCCAGGCGGGTCACTGCCCCTGCCCACGCCAATCTCCAGTGAAGCTGGTG  120
121  TTGAGAAGCGCGGTAGTGGTTTTGCAAATGCCGTCTACTTCACCAACTGGGGCATTTATG  180
181  GCCGCAACTTCCAGCCTGCCGACCTTCCTGCCTCGGAGATTACTCACGTACTCTACTCCT  240
241  TCATGAATGTCCGCGCAGATGGCACCATCTTTTCCGGTGATATACCTATGCCGACTACGAGA  300
301  AGCACTACGCTGGTGACTCTTGGAACGATGTGGGCACGAACGCTTACGGTTGTGTTAAGC  360
361  AACTTTATCTTCTCAAGAAGCAGAACCGCAACATGAAGGTGATGCTGTGTCGATTGGTT  420
421  GGACATGGTCTACCAACTTCCCCGCTGCCGCCAGCTCGGCTGCTACCCGAAAGACTTTTG  480
481  CTCAGTCTGCTGTTGGCTTCATGAAGGCTCAGGGGTTTCGACGGTATTGATATCGACTGGG  540
541  AGTACCCCGCGATGCCACTCAGGCTCCAGAATATGGTTCTCTTGCTACAGGCTGTCCGCA  600
601  GTGAGCTCGACTCCTACGCTGCCCAGTACGCCAAGGGTCACCACTTCCTGCTTTCAATTG  660
661  CCGCCCCTGCTGGACCTGACAATTATAACAAGCTGAAGTTTGCTGAGCTTGGCAAGGTTC  720
721  TCGATTACATTAACCTCATGGCTTACGATTACGCTGGAGCAACTACACTGGCC  780
781  ACGATGCCAACATATACGCAAACCCGAGAACCCCACCCTTACAACACGGACG  840
841  ATGCTGTCCAGGCCCTATATCAACGGCGGCGTCCCTGCCAACAAGATCGTCCTTGGTATGC  900
```

FIG. 4B

```
            FROM FIG. 4A                                                                FROM FIG. 4A

901    CAATCTACGGCCGATCCTTCCAGCAAACCGAGGGTATCGGTAAGCCCTTACAATGGTATTG      960
 961    GCTCTGGTAGCTGGGAGAACGGTATCTGGGACTACAAGGCTCTCCCCAAGGCTGGTGCCA     1020
1021    CCGTCAAGTGCGACGATACCGCCAAGGATGCTACAGCTACGATCCAAGCACTAAGGAGC      1080
1081    TTATTTCTTTCGATACGCCCGGCTATGATCAGCACCAAAGTTAGCTGGCTCAAGGGCAAGG    1140
1141    GCCTTGGCGGCAGCATGTTCTGGGAGGCTTCTGCCGACAAAGAAGGGCTCGGACTCTCTTA    1200
1201    TTAGCACCAGCCACCAAGGTCTCGGTAGCCAGGACAGCACTCAGAACTACCTCGACTACC     1260
1261    CTAACTCCAAGTACGACAACATCAAGAAGGGCATGAACTAAGCAGTCGGTGTTTGCATAG     1320
1321    CTTGATTGATGCTCGACTCTAGAGGATCGAACTGTACCGAGCTC                     1364
```

FIG. 5A

```
   1  GGATCCATGAAGAAGAATAGGATGATGATGATGGAGCGTAGGAGTGGTGTGGATG   60
  61  CTGTTGTTGGTTGGAGGAAGCTACGGAGGTAGTGGTTTTGCAAATGCCGTCTACTTCACC  120
 121  AACTGGGGCATTTATGCCGCAACTTCCAGCCTGCCGACCTTCCTGCCTCGGAGATTACT  180
 181  CACGTACTCTACTCCTTCATGAATGTCCGCGCAGATGGCACCATCTTTTCCGGTGATACC  240
 241  TATGCCGACTACGAGAAGCACTACGCTGGTGACTCTTGGAACGATGTGGGCACGAACGCT  300
 301  TACGGTGTGTTAAGCAACTTTATCTTCTCAAGAAGCAGAACCGCAACATGAAGGTGATG  360
 361  CTGTCGATTGGTGGTTGGACATGGTCTCTGTGGCTTGGCTTCATGAAGGACTCGGCTGCT  420
 421  ACCCGAAAGACTTTTGCTGGGAGTACCCCGCGATGCCACTCAGGCTGACTCCCAGTACGC  480
 481  ATTGATATCGACTGGGAGCTCGACTGCCAGTGAGCTCCTGCGACCTGCCCAGTACGCCAAGGGTCACCAC  540
 541  CTACAGGCTGTCCGCAATTGCCGCCGCTGGACCTGACAATTATAACAAGCTGAAGTTTGCT  600
 601  TTCCTGCTTTCAATTGCCGCCGCTGGACCTGACAATTATAACAAGCTGAAGTTTGCT  660
 661  GAGCTTGGCAAGGTTCTCGATTACATTAACCTCATGGCTTACGCTGGATCTTGG  720
 721  AGCAACTACACTGGCCACGATGCCAACATATACGCAAACCCGCAGAACCCCAACGCCACC  780
 781  CCTTAACACACGGACCGTGTCCAGGCCTATATCAAGGCCGTCCCTGCCAACAAG  840
 841  ATCGTCCTTGGTATGCCAATCTACGGCCGATCCTTCCAGCAAACCGAGGGTATCGGGTAAG  900
```

FIG. 5B

```
↑ FROM FIG.5A                                                    FROM FIG.5A ↑

901  CCTTACAATGGTATTGGCTCTCTGGTAGCTGGGAGAACGGTATCTGGGACTACAAGGCTCTC    960
 961  CCCAAGGCTGGTGCCACCGTCAAGTGCGACGATACCGCCAAGGATGCTACAGCTACGAT      1020
1021  CCAAGCACTAAGGAGCTTATTTCTTTCGATACGCCGGCTATGATCAGCACCAAAGTTAGC     1080
1081  TGGCTCAAGGGCAAGGGCCTTGGCGGCAGCATGTGTTCTGGGAGGCTTCTGCCGACAAGAAG   1140
1141  GGCTCGGACTCTCTTATTAGCACCAGCCACCAAGGTCTCGGTAGCCAGGACAGCACTCAG     1200
1201  AACTACCTCGACTACCCTAACTCCAAGTACGACAACATCAAGAAGGGCATGAACTAAGCA     1260
1261  GTCGGGTGTTTGCATAGCTTGATTGCTCGACTCTAGAGGATCGAACTGTACCGAGCTC       1320
```

5,446,138

RECOMBINANT DNA CODING FOR A PROTEIN WITH ENDOCHITINASE ACTIVITY

BACKGROUND OF THE INVENTION

The invention relates to a novel recombinant DNA coding for a novel protein with endochitinase activity or for a precursor thereof, to a bacterium, a yeast or a fungus containing this recombinant DNA, to a plant cell, a plant or a part of a plant, in particular a plant seed, containing this recombinant DNA, to a method of rendering plants resistant to pathogens such as fungi and bacteria, as well as arthrepods, especially insects, and nematodes, which comprises a step involving transformation by this gene, to this novel protein and to a process for its preparation.

Cultivated plants are subject to attacks by pathogens such as fungi and bacteria, as well as arthropods, especially insects, and nematodes, which are responsible for substantial losses of harvest. At the present time, the main means of controlling these pathogens is to use chemical substances with fungicidal or bactericidal activity. It is now known that plants react naturally to these attacks by means of various defense mechanisms which unfortunately are generally triggered too late and are too weak in intensity to be sufficiently effective. One of these mechanisms includes the induction of an enzyme called chitinase EC 3.2.1.14 (A. Toppan et al., 1982, Agronomie, 2, 829–834). This induction can be stimulated artificially by substances such as ethylene, the consequence of which is to increase the resistance of the treated plant to pathogens (Boller T., 1988, Oxford Surveys of Plant Molecular and Cell Biology, 5, 145–174).

Chitin is a linear polysaccharide polymer consisting of N-acetylglucosamine units joined by β-1,4 linkages. Said polymer is a structural compound present in the wall of most pathogenic fungi, in the exoskeleton of arthropods, especially insects, and in the outer envelope of the eggs and cysts of nematodes. Enzymes called chitinases are capable of degrading chitin. They are divided up into two different groups defined according to their mode of attacking chitin: exochitinases, which are capable of freeing the N-acetylglucosamine unit located at the non-reducing ends of the chains, and endochitinases, which are capable of fragmenting the chains and are the only chitinases capable of inhibiting the growth of mycelial hyphae in vitro (Roberts W. K. et al., 1988, Gen. Microbiol., 134, 169–176). The vast majority of the known plant chitinases are of the endo type, in contrast to the known bacterial chitinases, which are of the exo type (Roberts W. K. et al., 1988, Gen. Microbiol., 134, 169–176).

DNA sequences coding for bacterial exochitinases have already been isolated and cloned (Jones J. D. G. et al., 1986, EMBO J., 5, 467–473, and Sundheim L. et al., 1988, Physiol. Molec. Plant Pathol., 33, 483–491). U.S. Pat. No. 4,751,081 describes the isolation and cloning of the complete gene coding for the chitinase of Serratia marcescens and the transformation of the bacteria Pseudomonas fluorescens NZ130 and Pseudomonas putida MK280 by this gene. These transformed bacteria are capable of slightly degrading a colloidal chitin dispersed in the bacterial culture medium. The work of Harpster M. H. et al., 1989, Nucl. Ac. Res., 17, 5395, has shown that this gene codes for an exochitinase, which explains the low degradation efficacy observed (cf. Table 2, columns 13 and 14 of said document). The publication by Jones J. D. G. et al. (1988), Mol. Gen. Genet., 212, 536–542, mentions the transformation of tobacco plants by Agrobacterium tumefaciens containing a chimeric gene comprising the coding part of the exochitinase of Serratia marcescens, under the control of different plant promoters. Said document gives no indication of any increase in the pathogen resistance conferred by the expression of this exochitinase.

Genomic DNA and/or complementary DNA sequences coding for certain plant endochitinases have also been isolated and cloned (Bfoglie K. E., 1986, Proc. Ntl. Acad. Sci. USA, 83, 6820–6824, and Hedrick S. A., 1988, Plant Physiol., 86, 182–186).

International patent application 90/07001 describes the construction of a plasmid carrying a complementary DNA of the endochitinase of the bean Phaseolus vulgaris under the control of a strong promoter, transformation with the aid of Agrobacterium tumefaciens, the regeneration of the transformed tobacco, experiments showing the enhanced resistance of the regenerated plants to the fungi Rhizoctonia solani and Botrytis cinerea, the production of transgenic tomato plants expressing the bean chitinase and the production, with the aid of this gene, of transgenic colza plants having an enhanced level of chitinase activity and an enhanced resistance to Rhizoctonia solani compared with the non-transformed colza plants.

A genomic DNA and/or complementary DNA sequence coding for a chitinase of a filamentous fungus has never been isolated hitherto. The only partially isolated and characterized chitinase of a filamentous fungus is the endochitinase of Aphanocladium album (Kuntz, 1991— Doctoral Thesis at the Université de P. et M. Curie—Paris).

SUMMARY OF THE INVENTION

The present invention relates to a novel recombinant DNA which codes for a protein with endochitinase activity or for a precursor thereof, this protein with endochitinase activity comprising the following amino acid sequence (a1)(SEQ ID NO:1):

Gly Ser Gly Phe Ala Asn Ala Val Tyr Phe Thr Asn Trp Gly Ile
1               5                   10                  15

Tyr Gly Arg Asn Phe Gln Pro Ala Asp Leu Pro Ala Ser Glu Ile
        20                  25                  30

Thr His Val Leu Tyr Ser Phe Met Asn Val Arg Ala Asp Gly Thr
        35                  40                  45

Ile Phe Ser Gly Asp Thr Tyr Ala Asp Tyr Glu Lys His Tyr Ala
        50                  55                  60

Gly Asp Ser Trp Asn Asp Val Gly Thr Asn Ala Tyr Gly Cys Val
        65                  70                  75

Lys Gln Leu Tyr Leu Lys Lys Gln Asn Arg Asn Met Lys Val
        80                  85                  90

Met Leu Ser Ile Gly Gly Trp Thr Trp Ser Thr Asn Phe Pro Ala
        95                  100                 105

Ala Ala Ser Ser Ala Ala Thr Arg Lys Thr Phe Ala Gln Ser Ala
        110                 115                 120

Val Gly Phe Met Lys Asp Trp Gly Phe Asp Gly Ile Asp Ile Asp
        125                 130                 135

Trp Glu Tyr Pro Ala Asp Ala Thr Gln Ala Gln Asn Met Val Leu
        140                 145                 150

-continued

Leu Leu Gln Ala Val Arg Ser Glu Leu Asp Ser Tyr Ala Ala Gln
          155                 160                 165

Tyr Ala Lys Gly His His Phe Leu Leu Ser Ile Ala Ala Pro Ala
          170                 175                 180

Gly Pro Asp Asn Tyr Asn Lys Leu Lys Phe Ala Glu Leu Gly Lys
          185                 190                 195

Val Leu Asp Tyr Ile Asn Leu Met Ala Tyr Asp Tyr Ala Gly Ser
          200                 205                 210

Trp Ser Asn Tyr Thr Gly His Asp Ala Asn Ile Tyr Ala Asn Pro
          215                 220                 225

Gln Asn Pro Asn Ala Thr Pro Tyr Asn Thr Asp Asp Ala Val Gln
          230                 235                 240

Ala Tyr Ile Asn Gly Gly Val Pro Ala Asn Lys Ile Val Leu Gly
          245                 250                 255

Met Pro Ile Tyr Gly Arg Ser Phe Gln Gln Thr Glu Gly Ile Gly
          260                 265                 270

Lys Pro Tyr Asn Gly Ile Gly Ser Gly Ser Trp Glu Asn Gly Ile
          275                 280                 285

Trp Asp Tyr Lys Ala Leu Pro Lys Ala Gly Ala Thr Val Lys Cys
          290                 295                 300

Asp Asp Thr Ala Lys Gly Cys Tyr Ser Tyr Asp PRo Ser Thr Lys
          305                 310                 315

Glu Leu Ile Ser Phe Asp Thr Pro Ala Met Ile Ser Thr Lys Val
          320                 325                 330

Ser Trp Leu Lys Gly Lys Gly Leu Gly Gly Ser Met Phe Trp Glu
          335                 340                 345

Ala Ser Ala Asp Lys Lys Gly Ser Asp Ser Leu Ile Ser Thr Ser
          350                 355                 360

His Gln gly Leu Gly Ser Gln Asp Ser Thr Gln Asn Tyr Leu Asp
          365                 370                 375

Tyr Pro Asn Ser Lys Tyr Asp Asn Ile Lys Gly Met Asn
          380                 385 or a sequence having a high degree of homology with the sequence (a1).

Here a high degree of homology denotes a homology (ratio of the identical amino acids to the total number of amino acids) of at least 60% and preferably of at least 80% of the amino acid sequences in the maximum homology alignment according to the optimal sequence alignment method of Needleman and Wunsch, 1970, J. Mol. Biol., 48, 443-453. This method is used especially in the UWGCG software from the University of Wisconsin: Devereux et al., 1984, Nucl. Ac. Res., 12, 8711-8721—option GAP.

The already known peptide sequence of a chitinase which is closest to the sequence (a1) is that of the chitinase of *Serratia marcescens* (Jones J. D. G. et al., 1986, EMBO J., 5, 467-473) with a homology of about 33% (Kuntz, 1991, Doctoral Thesis—Université de P. et M. Curie, Paris); the latter chitinase is an exochitinase.

This recombinant DNA can be used for the expression of this protein with endochitinase activity, either for the purpose of conferring an enhanced pathogen resistance on a plant or a part of a plant which expresses said protein, or for the purpose of producing this protein with the aid of eucaryotic cells, especially Ascomycetes such as yeast, for example *Saccharomyces cerevisiae*, or filamentous fungi, for example *Cryphonectria parasitica*, or plant cells, or procaryotic microorganisms such as, for example, *Escherichia coli*.

This recombinant DNA preferably comprises a signal sequence upstream of the sequence coding for the sequence (a1) or of the sequence having a high degree of homology with the sequence (a1); the function of this signal sequence, which is chosen according to the host cell, is to make it possible for the protein to be exported out of the cytoplasm.

For expression in procaryotic microorganisms such as, for example, *Escherichia coli*, this signal sequence can be either a sequence derived from a natural precursor of a protein exported by a procaryotic microorganism (for example the signal peptide OmpA (Ghrayeb et al., EMBO Journal, 3, 2437-2442) or that of alkaline phosphatase (J. Bact., 1983, 154, 366-374)), or a non-endogenous sequence originating from a eucaryotic precursor (for example the signal peptide of one of the natural precursors of human growth hormone), or a synthetic signal peptide (for example the one described in French patent application no. 2 636 643).

For expression in eucaryotic cells such as Ascomycetes, for example the yeast *Saccharomyces cerevisiae* or the filamentous fungus *Cryphonectria parasitica*, this signal sequence is preferably a sequence derived from a natural precursor of a protein secreted by these cells, for example, for the yeast, the natural precursor of invertase (European patent application 0 123 289) or that of the prepro-sequence of pheromone alpha (Danish patent application 2484/84), or, for *Cryphonectria parasitica*, that of the prepro-sequence of endothiapepsin, described in European patent application 475 842, of the sequence (SEQ ID NO:2):

Met Ser Ser Pro Leu Lys Asn Ala Leu Val Thr Ala Met Leu Ala
1                 5                   10                  15

Gly Gly Ala Leu Ser Ser Pro Thr Lys Gln His Val Gly Ile Pro
                  20                  25                  30

Val Asn Ala Ser Pro Glu Val Gly Pro Gly Lys Tyr Ser Phe Lys
                  35                  40                  45

Gln Val Arg Asn Pro Asn Tyr Lys Phe Asn Gly Pro Leu Ser Val
                  50                  55                  60

Lys Lys Thr Tyr Leu Lys Tyr Gly Val Pro Ile Pro Ala Trp Leu
                  65                  70                  75

Glu Asp Ala Val Gln Asn Ser Thr Ser Gly Leu Ala Glu Arg
                  80                  85

For expression in plant cells, the signal sequence used is either a sequence coding for the signal peptide of a plant cell protein which is known to be exported, for example that of tomato endochitinase (Doctoral Thesis in Sciences—specialty: plant molecular biology, 1986, by M. Durant—Université de Paris Sud), of the sequence (SEQ ID NO: 3):

Met Arg Arg Thr Ser Lys Leu Thr Thr Phe Ser Leu Leu Phe Ser
1                 5                   10                  15

Leu Val Leu Leu Ser Ala Ala Leu Ala
                  20 or that of bean endochitinase (Broglie K. E. et al., Proc. Natl. Acad. Sci. USA (1986), 83,6820-6824), of the following sequence (a5) (SEQ ID NO.28):

Met Lys Lys Asn Arg Met Met Met Met Ile Trp Ser Val Gly Val
1           5                        10                    15

Val Trp Met Leu Leu Leu Val Gly Gly Ser Tyr Gly
          20                    25 or a signal sequence coding for the signal peptide of the following sequence (a2)(SEQ ID NO:4):

ATGAAGAAGA ATAGGATGAT GATGATGATA TGGAGCGTAG GAGTGGTGTG GATGCTGTTG 60

TTGGTTGGAG GAAGCTACGG A                                          81

Met Leu Ser Phe Val Lys Lys Ser Ile Ala Leu Val Ala Ala Leu
1           5                        10                    15

Gln Ala Val Thr Ala Leu Ala
                20 it being possible, if appropriate, for the signal peptide coded by the signal sequence to be separated from the sequence (a1) in the coded protein by one or more amino acids, in particular by the peptide of the following sequence (a3)(SEQ ID NO:5):

Thr Pro Ile Ser Ser Glu Ala Gly Val Glu Lys Arg
1           5                        10

The amino acid sequences (a1), (a2) and (a3) can be coded for example by the following nucleotide sequences (Na1), (Na2) and (Na3):

(Na1)(SEQ ID NO:6):

GGTAGTGGTT TTGCAAATGC CGTCTACTTC ACCAACTGGG GCATTTATGG CCGCAACTTC   60
CAGCCTGCCG ACCTTCCTGC CTCGGAGATT ACTCACGTAC TCTACTCCTT CATGAATGTC  120
CGCGCAGATG GCACCATCTT TTCCGGTGAT ACCTATGCCG ACTACGAGAA GCACTACGCT  180
GGTGACTCTT GGAACGATGT GGGCACGAAC GCTTACGGTT GTGTTAAGCA ACTTTATCTT  240
CTCAAGAAGC AGAACCGCAA CATGAAGGTG ATGCTGTCGA TTGGTGGTTG GACATGGTCT  300
ACCAACTTCC CCGCTGCCGC CAGCTCGGCT GCTACCCGAA AGACTTTTGC TCAGTCTGCT  360
GTTGGCTTCA TGAAGGACTG GGGTTTCGAC GGTATTGATA TCGACTGGGA GTACCCCGCC  420
GATGCCACTC AGGCTCAGAA TATGGTTCTC TTGCTACAGG CTGTCCGCAG TGAGCTCGAC  480
TCCTACGCTG CCCAGTACGC CAAGGGTCAC CACTTCCTGC TTTCAATTGC CGCCCCTGCT  540
GGACCTGACA ATTATAACAA GCTGAAGTTT GCTGAGCTTG GCAAGGTTCT CGATTACATT  600
AACCTCATGG CTTACGATTA CGCTGGATCT TGGAGCAACT ACACTGGCCA CGATGCCAAC  660
ATATACGCAA ACCCGCAGAA CCCCAACGCC ACCCCTTACA ACACGGACGA TGCTGTCCAG  720
GCCTATATCA ACGGCGGCGT CCCTGCCAAC AAGATCGTCC TTGGTATGCC AATCTACGGC  780
CGATCCTTCC AGCAAACCGA GGGTATCGGT AAGCCTTACA ATGGTATTGG CTCTGGTAGC  840
TGGGAGAACG GTATCTGGGA CTACAAGGCT CTCCCCAAGG CTGGTGCCAC CGTCAAGTGC  900
GACGATACCG CCAAGGGATG CTACAGCTAC GATCCAAGCA CTAAGGAGCT TATTTCTTTC  960
GATACGCCGG CTATGATCAG CACCAAAGTT AGCTGGCTCA AGGGCAAGGG CCTTGGCGGC 1020
AGCATGTTCT GGGAGGCTTC TGCCGACAAG AAGGGCTCGG ACTCTCTTAT TAGCACCAGC 1080
CACCAAGGTC TCGGTAGCCA GGACAGCACT CAGAACTACC TCGACTACCC TAACTCCAAG 1140
TACGACAACA TCAAGAAGGG CATGAAC                                    1167

(Na2)(SEQ ID NO:7):

ATGTTGAGCT TTGTCAAAAA GTCGATCGCC TTGGTGGCGG CCCTGCAGGC GGTCACTGCC   60
CTGGCC                                                              66

(Na3)(SEQ ID NO.8):

ACGCCAATCT CCAGTGAAGC TGGTGTTGAG AAGCGC                            36

The amino acid sequence (a5) can be coded for example by the following nucleotide sequence (Na5) (SEQ ID NO:29):

The invention further relates to a unit for expressing the recombinant DNA defined above, said unit advantageously being carried by a vector called an expression vector.

For expression in procaryotic microorganisms, in particular in *Escherichia coli*, the recombinant DNA must be inserted into an expression unit containing especially an effective promoter, followed by a ribosome binding site upstream of the gene to be expressed, and an effective transcription termination sequence downstream of the gene to be expressed. This unit must also contain a selection marker or be introduced into the host cell at the same time as a unit for expressing a selection marker (for example with the aid of an expression vector which carries these two units). All these sequences must be chosen according to the host cell.

For expression in eucaryotic cells such as Ascomycetes, the expression unit according to the invention comprises the above-defined recombinant DNA together with the means necessary for its expression.

For expression in Ascomycetes cells such as yeast, for example *Saccharomyces cerevisiae*, it is necessary to insert the recombinant DNA between sequences recognized as an effective promoter, on the one hand, and a transcription terminator, on the other. The expression unit carries a selection marker or is introduced into the host cell at the same time as a selection marker. This selection marker is preferably an auxotrophic marker (which complements a mutation of the recipient cells), making it possible to select those cells which have integrated the recombinant DNA in a large number of copies, either into their genome or into a multicopy vector.

For expression in Ascomycetes cells such as those of filamentous fungi, for example of the genera Aspergillus, Neurospora, Podospora, Trichoderma or Cryphonectria, the expression unit according to the invention carries the above-defined recombinant DNA together with the means necessary for its expression, and, if appropriate, a selection marker and/or telomeric sequences. It is in fact possible to select those transformants which have integrated a DNA of interest with the aid of a selection marker located either on the same unit as the DNA of interest or on another unit, these two units then being introduced by cotransformation. The recombinant DNA of the invention can be either integrated into the genome of the filamentous fungi or conserved in extrachromosomal form by means of sequences permitting the replication and partition of this DNA.

For expression in plant cells, it is necessary to insert the above-defined recombinant DNA between an effective promoter and an effective terminator in the plants.

The promoter is preferably a strong constitutive promoter, for example the 35S promoter of cauliflower mosaic virus, or a promoter which controls specific tissue or organ expression, such as the promoter of the small subunit of ribulose-1,5-bisphosphate carboxylase-oxygenase, which is expressed preferentially in the leaves and very particularly in the tissues of the mesophyll (Kuhlemeier et al., 1987, Ann. Rev. Plant Physiol., 38: 221–257). It is also possible to use a specific promoter which controls expression for example in the seeds or during a precise stage of the development of the plant, or a promoter which can be induced following a heat shock, a wound or interaction between the plant and parasites (Kuhlemeier et alo, 1987, op. cit.) if expression of the recombinant DNA is sought in these situations.

The terminator sequence, containing polyadenylation sites, is used, which can be isolated from plant genes or from genes which are expressed in plants, such as, for example, the terminator of the nopaline synthase of *Agrobacterium tumefaciens*.

The invention further relates to a bacterium, for example of the species *Escherichia coli*, a yeast, for example *Saccharomyces cerevisiae*, or a filamentous fungus, for example *Cryphonectria parasitica* or *Fusarium oxysporum*, which contains the above-defined recombinant DNA together with the means necessary for its replication and its expression. This bacterium, this yeast or this filamentous fungus can be used in the preparation of a protein with endochitinase activity.

The invention further relates to a bacterium, for example of the species *Escherichia coli*, which contains the above-defined recombinant DNA together with the means permitting its replication, and which can therefore be used for cloning this recombinant DNA, and to a bacterium which is capable of infecting a plant with the transfer of genetic material, for example from one of the species *Agrobacterium rhizogenes* and *Agrobacterium tumefaciens*, which contains this DNA in a context permitting its replication and which can therefore be used for 5 transforming plant cells. The transformation of plant cells by the above recombinant DNA can also be effected by another biological method such as the pollen tube method (Zhong-xun Luo et al., Plant Molec. Biol. Rep., 1988, 6, 165–176) and the direct transformation of germinating seeds (Toepfer R. et al., 1989, The Plant Cell, 1, 133–139), or by a physical method such as the use of polyethylene glycol, electroporation (Chistou P. et al., 1987, Proc. Ntl. Acad. Sci. USA, 84, 3662–3699) and bombardment with microprojectiles (Klein T. M. et al., 1988, Proc. Ntl. Acad. Sci. USA, 85, 8502–8505).

The invention further relates to a plant cell which is transformed by the above-defined recombinant DNA together with the means necessary for its expression. This plant cell can originate from a major crop species such as, for example, maize, soya, beet, wheat, barley, poppy, colza, sunflower, alfalfa and sorghum, a flower species such as rose, carnation and gerbera, or a vegetable species such as carrot, tomato, lettuce, chicory, pimento, melon and cabbage. Species of particular value are the colza *Brassica napus*, the sunflower *Helianthus annuus* and the tobacco *Nicotiana tabacum*.

The transformation step, which involves one cell or a few cells, is followed by a step for multiplication of these transformed cells to give calluses, which can produce transformed plants by processes of organogenesis or embryogenesis.

The invention therefore further relates to a plant or a part of a plant which contains the above-defined recombinant DNA together with the means necessary for its expression. A particularly valuable part of a plant is the part which is capable of forming a complete new plant, especially after sowing, burying or pricking out, or of producing seeds. Such a part is for example a grain, a seed, a cutting, a runner, etc. These plants can be any one of the above species and more particularly the species *Nicotiana tabacum*, *Helianthus annuus* and *Brassica napus*.

The invention further relates to a method of obtaining plants resistant to parasites such as phytopathogenic fungi and bacteria, as well as arthropods, especially insects, and nematodes, which comprises a step for the transformation of plant cells by this recombinant DNA, followed by a step for multiplication of the transformed cells and a step for regeneration of the plants.

The step for transformation of the plant cells is preferably carried out in vitro with the aid of an agrobacterium (i.e. a bacterium of the genus Agrobacterium) which has integrated the recombinant DNA of interest.

The invention further relates to the pathogen-resistant plants which can be obtained by means of the above-defined method.

The invention further relates to the use of a plant containing the above-defined recombinant DNA together with the means necessary for its expression, as the genetrix in a selection program for creating new plant varieties.

The invention further relates to a novel protein with endochitinase activity which can be obtained with the aid of the above-defined recombinant DNA. This protein preferably comprises the sequence (a1) or a sequence having a high degree of homology with the sequence (a1). It advantageously has an apparent molecular weight of 39±3 or 41±3 kDa. It can be N-glycosylated if it is expressed in a cell which permits glycosylation.

This protein is of interest as the active principle of a novel drug for the treatment of complaints such as, for example, mycoses.

The invention further relates to a process for the preparation of this protein, which comprises culturing plant cells, plant calluses, plants or parts of plants containing the above-defined recombinant DNA, lyzing them and isolating and purifying this protein.

The invention will be understood more clearly with the aid of the following description, divided up into sections, which comprises experimental results and a discussion thereof. Some of these sections concern experiments performed with the aim of putting the invention into effect, and others concern practical Examples of the invention, which of course are given purely by way of illustration.

The techniques below, which are well known to those skilled in the art, are all largely explained in detail in the work by Sambrook et al.: "Molecular Cloning: A Laboratory Manual" published in 1989 by Cold Spring Harbor Press in New York (2nd edition).

BRIEF DESCRIPTION OF THE DRAWINGS

The following description will be understood more clearly with reference to FIGS. 1 to 5.

FIGS. 1(A), 1(B) and 1(C) (SEQ ID NO:9) show the nucleotide sequence of the full length complementary DNA coding for the chitinase of *Aphanocladium album* and the peptide sequence of the translated protein, the cleavage site between the pre-peptide sequence and the pro-peptide sequence, and the cleavage site between the pro-peptide sequence and the mature protein, being represented by arrows underneath the peptide sequence, the different restriction sites used in the subsequent constructions being indicated by a broken vertical line above the nucleotide sequence, and the potential N-glycosylation sites being underlined.

FIGS. 2(A), 2(B), 2(C) and 2(D) (SEQ ID NO:11) show the nucleotide sequence of the genomic DNA coding for the chitinase of *Aphanocladium album*, the nucleotides of the introns being shown in lower case, and the peptide sequence of the translated protein.

FIG. 3 (SEQ ID NO:1) shows the peptide sequence of the mature protein.

FIGS. 4(A) and 4(B), 5(A) and 5(B) (SEQ ID NOS:13–14) respectively show the sequences coding for the chitinase of *A. album* in plasmids pBR61 and pBR62 respectively (vectors for expression in plant cells), bordered by the BamHI and SacI restriction sites.

DESCRIPTION OF THE PREFERRED EMBODIMENTS

Section 1 : Preparation of antibodies against the chitinase of *Aphanocladium album* a) Purification of the chitinase of *Aphanocladium album*

A chitinase of the filamentous fungus *Aphanocladium album* was purified to homogeneity from *A. album* culture medium as described below:

The *Aphanocladium album* strain used is the overproductive mutant of chitinase $E_3$ obtained by UV mutagenesis of the wild-type strain ETHM 483 according to the protocol described by Vasseur et al., 1990, J. Gen. Microbiol., 136, 12, 2561–2568. This strain was cultivated on a malt-agar medium under the conditions described by Forrer H. R., Phytopath. Z., 88, (1977), 306. Fragments taken from this culture are used to inoculate a liquid culture medium containing 1% of chitin (Srivastava A. K. et al., Experientia, 41, (1985), 1612–1613). The protein is purified from the culture medium by liquid chromatography according to Pharmacia's FPLC technique on a cation exchange column based on synthetic polymer (Mono S from Pharmacia), and exclusion chromatography (molecular sieve chromatography) on a crosslinked agarose according to the protocol described below:

Step 1

The culture medium is concentrated 40-fold against polyethylene glycol (Carbowax 20M—Touzart et Matignon) and then dialyzed overnight at 4° C. against a 100 mM sodium acetate buffer solution of pH 5.0. The total amount of proteins is determined by Bradford's method (Bradford M. M., 1976, Anal. Biochem., 72, 248–254).

Step 2

The concentrated culture medium is then fractionated by chromatography on an ion exchange column based on synthetic polymer (Mono S column from Pharmacia) according to Pharmacia's FPLC technique. The extract, diluted beforehand in a 10 mM sodium acetate buffer solution of pH 5.2, is deposited on the MONO S column (HR 5/5) equilibrated with a 10 mM sodium acetate buffer of pH 5.2. The proteins retained on the column are eluted by a linear gradient of 10 to 500 mM sodium acetate of pH 5.2.

Step 3

The fractions containing the chitinase of *Aphanocladium album* are concentrated by ultrafiltration on a Centricon 10 membrane (Amicon). Purification of the protein is continued by exclusion chromatography on a crosslinked agarose (Superose 12 column from Pharmacia), elution being carried out with a 500 mM sodium acetate buffer solution of pH 5.2.

At each step the chitinase is identified by its molecular weight (electrophoresis on a 12.5% polyacrylamide gel in the presence of SDS—developing with silver) and its enzymatic activity is measured by the radiochemical method described below using tritium-labeled chitin as the substrate (Molano et al., (1977), Anal. Biochem., 83, 648–656).

When purification is complete, a protein with an apparent molecular weight of 41±3 kDa is isolated which has endochitinase activity (thesis by C. Kuntz, Université de Pierre et Marie Curie, 1991). This protein possesses chitinolytic activity, which is measured by the radiochemical method described below using tritium.

b) Characterization of the chitinase of *Aphanocladium album* b1. Measurement of the enzymatic activity of the chitinase of *Aphanocladium album*

The endochitinase activity of the chitinase is measured by a radiochemical method which makes it possible to estimate the amount of monomers or oligomers freed by the enzyme from a substrate (tritiated chitin). This method, which is described by Molano et al. (1977, Anal. Biochem., 83, 648–656), is summarized below.

50 μl of tritiated chitin of specific activity 0.58 MBq/ml are added to a volume of 10 μl of protein extract. The final volume is adjusted to 300 μl with 0.2M sodium acetate buffer of pH 5.0. After incubation for 90 min at 30° C., the chitin hydrolysis reaction is stopped with 100 μl of 20% trichloroacetic acid. The test tubes are then centrifuged for 10 min at 12,000 g. A 100 μl aliquot of the supernatant, containing the soluble oligomers of chitin, is removed and the corresponding radioactivity is measured by liquid scintillation in the presence of 5 ml of scintillating mixture. The specific chitinolytic activity is expressed in dpm/μg of protein.

b2. Determination of the amino-terminal sequence of the chitinase of *Aphanocladium album*

The amino-terminal end of the isolated protein was sequenced as described below. The samples to be treated are placed on the surface of a PVDF (polyvinylidene difluoride) filter, which is introduced into a protein sequencer (model 470 A, marketed by Applied Biosystems USA) equipped with a chromatograph (model 430 from Applied Biosystems), which continuously analyzes the phenylthiohydantoic derivatives formed after each degradation cycle.

The amino-terminal sequence determined is as follows (amino acids 1-23 of SEQ ID NO:1):

```
Gly Ser Gly Phe Ala Asn Ala Val Tyr Phe Thr Asn Trp Gly Ile
1             5              10                15

Tyr Gly Arg Asn Phe Gln Pro Ala
            20
``` c) Preparation of polyclonal antibodies

To prepare an immune serum, rabbits were injected with 25 μg of purified chitinase in 500 μl of Freund's complete adjuvant. Three booster injections of 25 μg in Freund's incomplete adjuvant (500 μl) were given at 3-week intervals. The immune serum was taken 3 weeks after the last injection.

This immune serum specifically recognizes the chitinase of *Aphanocladium album*. It enables the latter protein to be developed especially by the Western blot technique (described in section 8) from a total protein extract of an *Aphanocladium album* strain cultivated under the conditions described above.

Section 2: Construction of the complementary DNA library of *Aphanocladium album* a) Preparation of messenger RNAs extracted from *Aphanocladium album*

The total RNAs of the mycelium of the above *Aphanocladium album* strain, cultivated for 2 days on a medium in the presence of 1% of chitin, were extracted according to the method of Logeman et al., Analytical Biochemistry, 1987, 163, 16–20.

The mycelium is separated from the culture medium by filtration, washed with sterile water and then ground in a mortar in liquid nitrogen; the total RNAs are then extracted by the guanidine hydrochloride method in accordance with the recommendations of Logeman et al. (op. cit.). After an ethanolic precipitation step, the total RNAs are dissolved in a buffered solution.

The poly(A)+ messenger RNAs were isolated after 2 chromatography cycles on a column of oligo (dT) cellulose as described by Sambrook et alo (op. cit.). The messenger RNAs (mRNAs) are quantified by spectrophotometry at 260 nm.

b) Synthesis of the complementary DNAs

The complementary DNAs were synthesized with the aid of the "Riboclone cDNA Synthesis System" kit from Promega (ref. C2100) in accordance with the supplier's recommendations. This kit uses the method described by Okayama et al., 1982, Mol. and Cell. Biol., 2, 161–170, and modified by Gübler and Hoffman, 1983, Gene, 25, 263–269, which favors the synthesis and cloning of complete cDNAs. The complementary DNAs were cloned at the EcoRI site into vector λgt11 by following the procedure of the cloning system from Amersham (cDNA cloning system kit, ref. RPN 1280). The number of recombinants was then estimated by counting the lysis plates obtained on a tapetum of bacteria of the strain *E. coli* Y 1090 (Sambrook et al., op. cit.). About $10^5$ clones were obtained, 80% of which are recombinant clones.

Section 3: Immunoscreening of the complementary DNA library constructed from the messenger RNAs of *Aphanocladium album*

The construction of a library in vector λgt11 makes it possible to express the cloned cDNAs in the form of proteins coded by the mRNAs which were used to construct this library. This synthesis takes place after induction with isopropyl thio-β-D-galactoside (IPTG); the synthesized proteins can then be recognized by previously obtained antibodies against the desired protein (section 1). The clones can be identified and isolated according to a protocol known to those skilled in the art and described for example by Sambrook et al. (op. cit.).

The library is amplified by infection of the strain *E. coli* Y 1090 with a suspension of phages containing $10^4$ particles capable of forming lysis plates. This step is carried out in Petri dishes of diameter 90 mm. Incubation is carried out at 42° C. for 16 h and permits a $10^7$-fold amplification.

The amplified library is then plated out on a taperum of bacteria of the strain *E. coli* Y 1090 at a density of $10^5$ particles capable of forming lysis plates. The bacteria are plated out in 5 Petri dishes of diameter 150 mm and incubated at 42° C. for 5 h. A cellulose filter (Schleicher and Schuell, BA 85) impregnated with IPTG (10 mM) is laid on the surface of the dishes and left in contact with the gelose medium for 5 h at a temperature of 37° C.; it is then replaced with a second filter, which is left on the same medium for 16 h. The filters are treated with a so-called blocking buffer composed of 10% of powdered milk (Regilait) in TNT buffer (10 mM Tris pH 8.0, 150 mM NaCl, 0.05% Tween), for 30 min, and incubated with the antiserum described above, diluted to 1/100 in TNT medium. The protocol for incubation and developing with alkaline phosphatase is the one described by the "Protoblot immunoscreening system" from Promega, ref. S3710. The positive clones appear blue-violet in color after developing.

The positive lysis plates, i.e. those corresponding to clones which synthesize chitinase, are then identified on the Petri dish and the bacteriophages are removed for purification by means of a secondary immunoscreening, conducted in a strictly identical manner to the primary screening which has just been described. Seventeen clones were obtained, corresponding to 7 different hybridization groups. One hybridization group, comprising 9 clones of about 230 bp, produces a particularly strong signal. One of these clones, called CH3C, was retained for the remainder of the study.

The DNA sequence of the CH3C clone was determined according to the deoxyribonucleotide method (Sanger et al., 1977, Proc. Ntl. Acad. Sci. USA, 14, 5463–5467). This clone does not contain the "full length" complementary DNA because its size is too small.

Section 4: Construction of the genomic DNA library of Aphanocladium album a) Preparation and encapsidation of the total DNA of Aphanocladium album The total DNA was prepared by the method of Daboussi et al., Curr. Genet., (1989), 15, 453–456. The DNA of A. album was then partially digested with the restriction enzyme Sau3AI and fractionated according to size on a sucrose gradient. The fragments with a size of between 12 and 20 kb were inserted into phage EMBL4 after cleavage of the latter at the BamHI site. Encapsidation in the phage particles is carried out in vitro using the "cDNA cloning system" kit from Amersham, ref. RPN.1280, and transfection is carried out on a tapetum of bacteria of the strain E. coli LE 292 (Sambrook et al., op. cit.). The library has a size of $1.2 \times 10^6$ plates and possesses 50% of recombinant phages.

b) Screening of the genomic library of Aphanocladium album b1. Preparation of the replicas on filters After amplification of the library by infection of the strain E. coli NM 539 (Sambrook et al., op. cit.) according to the techniques known to those skilled in the art, $10^5$ phages are plated out at a density of 20,000 particles capable of forming lysis plates per dish on a taperum of bacteria of the strain NM 539. Incubation takes 16 h at 37° C. The dishes are cooled and 2 replicas are made by successively laying 2 nylon filters (Hybond N, Amersham, ref. RPN 203N) on the dishes. The first filter is left in contact with the lysis plates for 45 s and the second for 90 s.

The replicas on membranes are laid, with the DNA facing upwards, on a sheet of Whatman 3MM paper saturated with a denaturing solution of the following composition: NaOH 0.5 M, NaCl 1.5 M, for 7 min, which makes it possible to fix the DNA. The replicas on membranes are then placed on a second sheet of Whatman 3MM, saturated this time with a neutralizing solution of the following composition: NaCl 1.5M, Tris-HCl pH 7.4 0.5M, for 3 min. The replicas on membranes are subsequently immersed in a $2 \times SSC$ solution (NaCl 0.30M, sodium citrate 0.030M) and then dried in the open air with the side which has fixed the DNA facing upwards.

b2. Preparation of the radioactive probe used to identify the positive clones, and hybridization of the replicas The probe used is the DNA of the CH3C clone obtained above (section 3), in which 100 ng of DNA are labeled with dCTPα$^{32}$p(3000 Ci/mmol, Amersham) by random labeling (random priming) using the labeling kit from Boehringer Mannheim GmbH (ref. 1004 760) in accordance with the manufacturer's recommendations. The specific activity obtained is $1 \times 10^9$dpm/μg of DNA.

The replicas on membranes are prehybridized for 1 h at 65° C. in a buffer of the following composition: $6 \times SSC$, $5 \times$ Denhardt's solution, 0.5% SDS and 100 μg/ml of sonicated salmon sperm DNA. The replicas on membranes are hybridized with the probe prepared above for 16 h in the same buffer and are subsequently washed for 20 min at 20° C. in a $2 \times SSC$, 0.1% SDS buffer, then for 40 min in a $2 \times SSC$, 0.1% SDS buffer at 65° C. and finally for 40 min in a $0.2 \times SSC$, 0.1% SDS buffer at 65° C., and are then dried and autoradiographed. Briefly, $20 \times SSC$ buffer contains 175.3 g/l of NaCl and 88.2 g/l of sodium citrate and is adjusted to pH 7 with a few drops of 10N NaOH. $10 \times$Denhardt's solution contains 1 g of Ficoll 400, 1 g of polyvinylpyrrolidone and 1 g of bovine serum albumin per 500 ml of final volume. Five phages were purified in three steps. Four of them have an identical digestion profile for the restriction enzymes EcoRI, HindIII and BamHI.

b3. Cloning and sequencing of a fragment containing a gene of Aphanocladium album coding for a chitinase The DNA of one of these 4 phages was digested with the enzyme BamHI. The restriction fragments obtained were separated by electrophoresis on 1% agarose gel. The DNA was transferred to a nylon filter (Hybond N$^+$, Amersham) according to the Southern blot method (Southern, E. M. (1975), J. Mol. Biol., 98, 503–517) and hybridized with the DNA of the CH3C clone labeled with dCTPα$^{32}$P(cf- section 4 b2). The membranes are then washed and developed according to the protocol recommended by Amersham, and autoradiographed with an XAR film (Kodak).

A very strong hybridization signal on a single band is detected. The size of this DNA fragment is estimated to be about 7 kb. This fragment, called fragment fBL1, is subsequently isolated by electroelution after electrophoresis according to the method described in the work "Plant Molecular Biology Manual", Gelvin et al., Kluwer Academic Press, 1988, and then ligated into a vector pUC13 opened at the BamHI site and dephosphorylated (Pharmacia, ref. 27-4969-01). The plasmid obtained is called plasmid pBL1. This vector is introduced into E. coli (DH5 αF') according to the protocol described by Sambrook et al., op. cit. The clone obtained is called BL1.

Sequencing

After preparation of the double-stranded DNA according to the techniques known to those skilled in the art, part of the insert of 7kb was sequenced according to the dideoxyribonucleotide method (Sanger et al., Proc. Ntl. Acad. Sci. USA, 14, 5463–5467, 1977) with the aid of the "T7sequencing kit" from Pharmacia, ref. 27-1 682-01.

The primer used is the oligonucleotide mixture of the formula below, called oligonucleotide mixture $N_1$, which corresponds to the sequences translated from the aminoterminal sequence of the purified protein (cf. section 1). This mixture was obtained by chemical synthesis with the aid of a Biosearch 4600 apparatus.

GGI TTT/C GCI AAT/C GCI GTI TAT/C TTT/C AC (SEQ ID NO:15)
Gly Phe    Ala  Asn    Ala  Val Tyr    Phe        (SEQ ID NO: 16)
(I represents inosine)

To be able to sequence the remainder of the strand, other primers were translated from the sequence obtained by means of these first primers. The sequence of the complementary strand was obtained by synthesizing primers in the reverse direction. It made it possible to confirm the sequence shown in FIGS. 2(A), 2(B) and 2(C), which will be commented upon in section 7.

Section 5: Preparation of a full length complementary DNA of the chitinase of *Aphanocladium album* a) Constitution of a complementary DNA library

The messenger RNAs isolated as described in section 2 were used to prepare a complementary DNA library in vector pTZ19R (marketed by Pharmacia). This vector is a plasmid comprising a polylinker containing unique restriction sites.

The cloning technique used is the one described by Caput et al., Proc. Ntl. Acad. Sci. (USA), (1986), 83, 1670–1674.

It consists on the one hand in digesting the vector with PstI, adding a polydC tail to the protuberant 3′ end and then digesting the resulting plasmid with BamHI. The fragment corresponding to the vector is purified on a column of Sepharose CL4B (Pharmacia). It therefore comprises a polydC tail at one end, the other end being a sticky end of the BamHI type. On the other hand, the messenger RNAs are subjected to reverse transcription starting from a primer with the following sequence (SEQ ID NO:17): 5′<GATCCGGGCCCT$_{(12)}$<3′. Thus, at their 5′ end, the cDNAs have the sequence GATC complementary to the BamHI sticky end.

The RNA-DNA hybrids obtained by the action of reverse transcriptase are subjected to alkaline hydrolysis, which makes it possible to remove the RNA. The single-stranded complementary DNAs are then purified by 2 cycles on a column of Sepharose CL4B and subjected to a treatment with terminal transferase so as to add polydGs at the 3′ end. The complementary DNAs are inserted in single-stranded form into the vector prepared as described above. A second oligonucleotide, called the adapter, complementary to the primer, is necessary for generating a BamHI sticky end at the 5′ end of the complementary DNAs. After hybridization of the vector, the complementary DNA and the adapter, the recombinant molecules are annealed by the action of the ligase of phage T4. The single-stranded regions are then made up to double-stranded regions by means of the DNA polymerase of phage T4.

The resulting pool of plasmids is used to transform the strain MC 1061 (Casabadan, Chou and Cohen, J. Bact. (1980), 143, 9971–9980) and the recombinant bacteria are selected for ampicillin resistance.

b) Screening of the library

Preparation of the labeled probes:

Three probes translated from the sequence of the CH3C complementary DNA clone and the BL1 genomic DNA clone (section 4) were synthesized with the aid of a Biosearch 4600 DNA synthesizer.

The probes are as follows:

(1) 5′ CAA ATG CCG TCT ACT TCA CC 3′ (SEQ ID NO:18)

(2) 5′ CCT CAT GGC TTA CGA TTA CG 3′ (SEQ ID NO:19)

(3) 5′ TCC AAC CTC GAG CAT CAA TC 3′ (SEQ ID NO:20)

They code respectively for sequences located at the start, in the middle and downstream of the coding sequence of the chitinase of *Aphanocladium album*. The probes are labeled by coupling with peroxidase.

Hybridization and detection of the colonies containing the complementary DNA of the chitinase of *Aphanocladium album*

About 100,000 colonies are screened by the in situ hybridization technique developed by Grunstein and Hogness (1975, Proc. Ntl. Acad. Sci. (USA), 72, 3961). About 10,000 bacteria are plated out on 10 Petri dishes to give isolated colonies. After incubation for 24 h at 37° C., each dish is replicated on 2 Hybond N+ nylon filters (Amersham), each filter being destined for treatment with the three probes.

The replicas on membranes are laid, with the colonies facing upwards, on a sheet of Whatman 3MM saturated with a solution of the following composition: NaOH 0.5M, NaCl 1.5M, for 5 min, and the membranes are then laid on a neutralizing solution of the following composition: NaCl 1.5M, Tris-HCl pH 8.0 0.5M, for 5 min. The replicas are then immersed in a 2×SSC solution (NaCl 0.30M, sodium citrate 0.030M).

The replicas on membranes are then treated with proteinase K (Boehringer Mannheim GmbH) at 100 μg/ml in a solution of the following composition: Tris-HCl 10 mM pH 8, EDTA 10 mM, NaCl 50 mM, SDS 0.1%, at a rate of 20 ml per membrane. Incubation is carried out for 30 min at 37° C., with shaking. The replicas on membranes are immersed again in a 2×SSC solution and the bacterial debris is partially removed by rubbing gently with a paper of trademark Kim Wipes. The membranes are then treated for 5 min in a 0.4M solution of NaOH and rinsed briefly in a 2×SSC solution to give two replicas on membranes for each dish.

The filters are placed in a buffer containing 0.1% SDS, 6×SSC, 10×Denhardt and 100 μg/ml of denatured sonicated salmon sperm DNA (Sigma) for prehybridization. The prehybridization temperature is 42° C. and the duration is 6 h.

Hybridization is carried out at 42° C. for 16 h by adding 60 ng/ml of the mixture of the 3 probes labeled with peroxidase.

The membranes are washed in 2×SSC solution +0.1% SDS, at 22° C. for 2 times 5 min and then for 30 min, followed by 2 washes of 15 min in 0.1×SSC solution +0.1% SDS, at 42° C., and finally for 3 min in 2×SSC solution at 22° C.

Developing is effected with the aid of the ECL kit from Amersham (ref. RPN2110) according to the manufacturer's protocol using Xomat AR films (Kodak).

35 colonies exhibited very strong hybridization with the mixture of the 3 probes.

The plasmid DNA of 15 of these 35 colonies was prepared and digested with the enzymes HindIII and BamHI. After electrophoresis on 1% agarose gel, double digestions make it possible to free a fragment with a size of about 1.6 kb in 4 out of the 15 cases.

Section 6: Determination of the sequence of the full length complementary DNA of the chitinase of *Aphanocladium album*

One of the 1.6 kb fragments was recloned into the DNA of the replicarive form of phage M13. The DNA of the M13 clones containing the 1.6 kb fragment was digested with exonuclease so as to generate a series of overlapping M13 clones ("Cyclone I Biosystem" procedure from IBI). Said clones were sequenced by the dideoxyribonucleotide method (Sanger et al., 1977, Proc. Ntl. Acad. Sci. USA, 14, 5463–5467).

a) Analysis of the cDNA sequence of the chitinase of *Aphanocladium album*

The following description will be understood more clearly with the aid FIGS. 1(A) and 1(B). This sequence contains a single open reading frame (not interrupted by a stop codon) compatible with the apparent molecular weight of the protein observed by electrophoresis on 12.5% polyacrylamide gel: the sequence starting with an ATG codon in position 97 and terminating with the TAA stop codon in position 1366, coding for a protein of 423 amino acids with a molecular weight of about 46 kDa.

A signal peptide is expected by those skilled in the art because chitinases are proteins which can be naturally secreted by fungus cells, requiring the presence of a signal peptide.

The UWGCG software from the University of Wisconsin: Devereux et al., 1984, Nucl. Ac. Res., 12, 8711–8721—option: Search for a signal peptide according to the method of G. Von Heijne, 1986, Nucl. Ac. Res., 14, 483–490, predicts in this sequence a part coding for a signal peptide recognized by eucaryotic or procaryotic cells, namely the following sequence (Na2)-(SEQ ID NO:7), called the pre-nucleotide sequence (starting with nucleotide 97 and terminating with nucleotide 162):

```
ATGTTGAGCT TTGTCAAAAA GTCGATCGCC TTGGTGGCGG CCCTGCAGGC GGTCACTGCC    60
CTGGCC                                                              66
``` coding for the signal peptide of 22 amino acids with the following sequence (a2) (SEQ ID NO: 4):

Met Leu Ser Phe Val Lys Lys Ser Ile Ala Leu Val Ala Ala Leu
1           5              10              15

Gln Ala Val Thr Ala Leu Ala
                20

Between the sequence coding for the above signal peptide and that coding for the mature protein, there is the following nucleotide sequence (Na3)(SEQ ID NO:8), called the pro-nucleotide sequence, starting with nucleotide 163 and terminating with nucleotide 198:

coding for the following peptide sequence (a3)(SEQ ID NO:5), called the pro-peptide sequence:

Thr Pro Ile Ser Ser Glu Ala Gly Val Glu Lys Arg
1           5              10

Upstream of the sequence coding for the mature chitinase of *Aphanocladium album*, there is therefore the sequence coding for the following prepro-peptide sequence (a4)(SEQ ID NO:21):

Met Leu Ser Phe Val Lys Lys Ser Ile Ala Leu Val Ala Ala Leu
1           5              10              15

Gln Ala Val Thr Ala Leu Ala Thr Pro Ile Ser Ser Glu Ala Gly
                20                  25                  30

Val Glu Lys Arg

The mature protein is the protein of 389 amino acids with a molecular weight of about 42.8 kDa which starts with the amino-terminal sequence determined in section 1. The observed apparent molecular weight of about 41±3 kDa corresponds, within the limits of experimental error, to the calculated molecular weight of 42.8 kDa of the protein translated from the complementary DNA. This protein possesses two potential N- glycosylation sites (underlined in FIGS. 1(A) and 1(B).

Comparison of the peptide sequence (a1) with the other peptide sequences already known The comparison was made with the class I, II and III plant chitinases defined by Shinshi et al., 1990, Plant Mol. Biol., 14, 357–368, and with the bacterial chitinases of *Bacillus circulans*, *Serratia marcescens* and *Streptomyces erythraeus*. The comparison was carried out with the aid of the UWGCG software from the University of Wisconsin: Devereux et al., 1984, Nucl. Ac. Res., 12, 8711–8721, option GAP. This algorithmic method considers all the possible alignments and creates an alignment in which the maximum number of identical amino acids are paired and the number of holes in the aligned sequences is minimized.

The peptide sequence closest to the sequence (a1) translated from the complementary DNA of *A. album* is that of the chitinase of *Serratia marcescens* (Jones J. D. G. et al., 1986, EMBO J., 5, 467–473) with a homology of about 33%. The latter chitinase is an exochitinase (Kuntz, 1991, Doctoral Thesis—Université de P. et M. Curie, Paris).

Section 7: Analysis of the genomic DNA sequence of the chitinase of *Aphanocladium album*

The following description will be understood more clearly with the aid of FIGS. 2(A), 2(B) and 2(C). The alignment of this sequence with the cDNA sequence of FIGS. 1(A) and 1(B) shows that this gene codes for the same peptide sequence as the cloned complementary DNA and reveals three small introns. The sequence starts with an ATG codon in position 126 and terminates with a TAA stop codon in position 1552. The first

```
ACGCCAATCT CCAGTGAAGC TGGTGTTGAG AAGCGC    36
``` intron starts in position 266 and terminates in position 320. The second intron starts in position 420 and terminates in position 472. The third intron starts in position 523 and terminates in position 571. This sequence codes for a protein of 423 amino acids.

Section 8: Expression of the chitinase of *Aphanocladium album* in *Fusarium oxysporum*

Cotransformation, which is based on the complementation of a recipient strain of the filamentous fungus *Fusarium oxysporum* f. sp. melonis of nitrate reductase minus (nia-) phenotype, is effected by mixing a plasmid carrying a gene coding for a nitrate reductase of *Aspergillus nidulans* and the above-defined plasmid pBL1 carrying the genomic DNA of the chitinase of *Aphanocladium album.* Selection of the transformants is carried out on a medium containing a source of nitrate, enabling only those transformants which have integrated the nitrate reductase gene to survive and develop. Some of these transformants also integrated the fBL1 fragment. The transformants which express chitinase activity are sought among these double transformants.

a) Transformation of *Fusarium oxysporum*

The recipient strain of *F. oxysporum* f. sp. melonis is the strain Fom150 nia9 described by Daboussi et al., 1989, Curr. Genet., 15, 453–456.

The niad gene coding for the nitrate reductase of *Aspergillus nidulans,* carried on a Sau3A fragment of 11 kb, is inserted into plasmid pFB39 derived from pUC19. This plasmid used for the transformation of *F. oxysporum* has the name pAN301. Its construction is described by Malardier et al., 1984, Gene, 78: 147–156.

Cotransformation is effected using a mixture of plasmid pAN301 and the above-described plasmid pBL1 in a ratio of 1/1. The experimental conditions used to ensure the transformation of the protoplasts of *F. oxysporum* and the selection of the transformants on nitrate are those described by LANGIN T. et al., (1990), Curr. Genet., 17: 313–319.

Four cotransformants, called Tr5, Tr6, Tr7 and Tr8, were obtained in this way.

b) Expression of the chitinase of *Aphanocladium album* by the cotransformants of *Fusarium oxysporum*

An analysis according to the Western blot method was performed on these 4 cotransformants in the manner described below. The proteins of the culture medium are concentrated against polyethylene glycol (Carbowax 20M—Touzart et Matignon) and the extract is subsequently dialyzed against a 0.2M sodium acetate buffer of pH 5.0 and then diluted in a loading buffer of the following composition:

0.125M Tris-HCl pH 6.8
4% sodium dodecylsulfate
20% glycerol
0.002% bromophenol blue
10% β-mercaptoethanol after which the mixture is heated at 100° C. for 10 min. 10 μg of solubilized proteins are deposited on an SDS-polyacrylamide electrophoresis gel according to the protocol described by Laemmli (Laemmli, Nature, 227, 1970, 680–685). After electrophoresis, the proteins of the gel are transferred to an Immobilon membrane (made of PVDF) by electrotransfer according to the technique of H. Towbin et al., Proc. Natl. Acad. Sci. USA, 76, 1979, 4350–4354.

Immunodetection is performed according to a protocol which comprises the following steps:

saturation of the PVDF membrane to which the proteins have been transferred by incubation for at least 2 h at 37° C. in a 3% solution of gelatin;
3 washes in phosphate buffered saline containing 0.05% of Tween 20 detergent;
incubation (for 1 h at 37° C.) in the presence of the previously prepared immune serum (containing the polyclonal antibodies recognizing the chitinase of *Aphanocladium album*) diluted to 1/10,000 in phosphate buffered saline;
3 washes in phosphate buffered saline containing 0.05% of Tween 20 detergent.

The antigen-antibody complex is then developed with the aid of a streptavidin-biotin system conjugated with alkaline phosphatase using the RPN 23 kit from Amersham ("Blotting detection kit") in accordance with the manufacturer's instructions.

For the cotransformants Tr8 and Tr7, the blot obtained shows the presence of a protein of about 41±3 kDa with the same apparent molecular weight as the purified chitinase of *A. album* obtained in section 1, which is absent from the control strain.

The non-expression for the cotransformants Tr5 and Tr6 probably results from insertion of the recombinant gene into a context which does not permit transcription.

The chitinase activity of the wild-type *F. oxysporum* strain (control) and that of the cotransformants Tr7 and Tr8 are measured by the radiochemical method of Molano et al. (1977, Anal. Biochem., 83, 648–656) summarized in paragraph (b) of section 1. The total amount of proteins is determined by Bradford's method (Bradford M. M., 1976, Anal. Biochem., 72, 248–254). The results are collated in Table (I) below. It is found that the culture medium of the cotransformant Tr8, which best expresses the chitinase of *A. album,* undergoes an increase in its specific chitinolytic activity by a factor of 25 to 30 compared with the control strain. Furthermore, the activity of the extracellular chitinase of the cotransformants Tr8 and Tr7 decreases when the anti-*A. album* chitinase antibodies (prepared in section 1) are added.

TABLE I

Comparison of the specific chitinolytic activity of the cotransformants Tr8 and Tr7, expressing the chitinase of *A. album*, with that of the control strain*

| | Specific chitinolytic activity (dpm/μg of protein) | | |
|---|---|---|---|
| | control strain | Tr8 | Tr7 |
| Exp1 | 52 | 1493 | 402 |
| Exp2 | 83 | 2019 | 760 |
| Exp3 | 83 | 135 | 157 |

*For each of these strains, two protein extracts of independent culture filtrates were prepared and their chitinolytic activity was determined 3 times independently by the radiochemical method of Molano et al.; the values shown in the Table represent the averages of these three measurements. Exp1 is the value obtained for the first extract and Exp2 is that obtained for the 2nd extract. Exp3 represents the value obtained for the first extract after it has been incubated for 1 h 30 min in the antichitinase serum prepared in section 1.

Section 9: Expression of the mature chitinase of *Aphanocladium album* in *E. coli* a) Construction of intermediate plasmid pEMR680

Plasmid pUC18 (Clontech), which comprises a polylinker carrying the PstI, SalI and BamHI sites in particular, is unwound by cleavage with the endonucleases PstI and SalI. The PstI-SalI fragment, carrying the origin of replication, is purified.

Cleavage of the cDNA (cf. section 6 and FIGS. 1(A) and 1(B) with the restriction enzymes PstI and XhoI generates a PstI-XhoI fragment of about 1250 base pairs. This fragment was purified on agarose gel and then ligated with the above PstI-SalI fragment with the aid of T4 polymerase (the SalI and XhoI sites disappear through ligation). The ligation mixture is used to transform the strain E. coli RRI.

The plasmid obtained is called plasmid pEMR680. This plasmid contains an incomplete fragment in its 5' part of the cDNA coding for the prepro-chitinase of *Aphanocladium album.* 47 base pairs are missing between the PstI site and the ATG codon marking the initiation of translation.

b) Construction of the vector for expression in *E. coli*: plasmid pEMR682

Partial hydrolysis of plasmid pEMR680 with the enzyme AccI and total hydrolysis with the enzyme BamHI makes it possible to free a fragment of about 1100 bp. This fragment codes for a 3' part of the coding sequence of the mature chitinase of *A. album* (cf. FIGS. 1(A) and 1(B)).

The synthetic oligonucleotide of the following sequence (Nt1)(SEQ ID NO:22):

```
5' TAT GGG TAG TGG TTT TGC AAA TGC CGT      3'
   A CCC ATC ACC AAA ACG TTT ACG GCA GA
``` makes it possible to reconstitute the 5' end of the mature chitinase of *A. album.* The first amino acid of the sequence of the mature protein (coded by GGT) is preceded by the sticky end of an NdeI site carrying an ATG translation initiation codon.

Plasmid pAR3040 (Studier F. U. et al., 1986, J. Mol. Biol., 189, 113–130) carries a pBR322 fragment comprising the origin of replication in *E. coli* and in the gene coding for ampicillin resistance, and a DNA fragment carrying the 10 gene of phage T7, as well as its promoter and its terminator. The 10 gene can easily be replaced with any other gene of interest since it is bounded by the sequences recognized by the restriction enzymes NdeI and BamHI.

Plasmid pAR3040 is hydrolyzed with the enzymes NdeI and BamHI, and the fragment carrying the origin of replication in *E. coli* and the ampicillin resistance gene, as well as the promoter and the terminator of the 10 gene of phage T7, is purified. Assembly by ligation of the oligonucleotide of sequence (Nt1), the 1100 bp fragment of plasmid pEMR680 and the fragment of plasmid pAR3040 produces, after transformation of the ligation mixture in the strain *E. coli* RRI, a plasmid called plasmid pEMR682.

c) Expression of the mature chitinase in *E. coli*

The promoter of the 10 gene of phage T7 is not recognized by the RNA polymerase of *E. coli.* It is therefore necessary to provide the strain *E. coli* RRI carrying plasmid pEMR682, called strain RRI/pEMR682, with an RNA polymerase which recognizes the promoter of the 10 gene of phage T7. The means which is chosen for carrying out this operation is to use the recombinant phage CE6 (Studier et al., op. cit.), which carries in its genome the gene coding for the RNA polymerase of phage T7.

Constitution of a stock of CE6 phages

This experiment, which is well known to those skilled in the art, is described by Sambrook et al., op. cit. It consists in infecting 100 μl of the bacterium ED 8739, cultivated in a medium containing 5 g of yeast extract, 10 g of bactotryptone, 5 g of NaCl, 10 mM MgSO4 and 0.4% of maltose, with phage CE6 so that the suspension is composed of 1 phage per 6 bacteria. This suspension is mixed with 3 ml of a medium called Top Agar having the same composition as that indicated above, but complemented with 7 g/l of agar. The mixture, kept at a temperature of 50° C., is plated out on a Petri dish containing the same medium, but complemented with 15 g/l of agar. After incubation overnight at a temperature of 37° C., the gelose is covered with lysis plates containing the phages. The phages are eluted by scraping off the Top Agar and mixing it with 3 ml of MgSO4 10 mM per Petri dish for 1 h at room temperature. The mixture is then centrifuged for 10 min at 15,000 g and the supernatant, which contains the phages at a concentration of $2.10^{10}$ phages per ml of supernatant, is called the phage stock. The phage stock is kept at a temperature of 4° C.

Expression of the chitinase

The strain RRI/pEMR682 is cultivated in a medium whose composition is identical to that of the medium used to prepare the phage stock, but without agar. After incubation at a temperature of 37° C., with shaking, this culture is diluted 50-fold in the same medium and incubated at a temperature of 37° C. to give a cell density of $10^9$ cells per ml (OD=1). The phages are added to the culture so that the mixture is composed of 10 phages per bacterium. The mixture is incubated for 2 h at a temperature of 42° C. The bacterial residue is then obtained by centrifugation for 10 min at 15,000 g.

d) Analysis of the chitinase produced

Polyacrylamide gel

A bacterial residue derived from a culture of 1 ml which has reached an optical density of 0.2, measured at 600 nm, is suspended in a buffer of the following composition: 0.125 mM Tris-HCl pH 6.8, 4% sodium dodecylsulfate, 20% glycerol, 0.002% bromophenol blue and 10% β-mercaptoethanol. The mixture is immersed for 10 min in boiling water, which makes it possible to lyze the bacteria and solubilize the proteins. The mixture is then subjected to electrophoresis on a 12.5% polyacrylamide gel (Laemmli U.K., 1970, Nature, 227, 680–685) in the presence of a size marker and the purified chitinase of *A. album* obtained in section 1. After decolorizetion of the gel, which has been stained with Coomassie blue beforehand, an additional band is found to exist for the strain RRI/pEMR682, representing approximately 20% of total proteins relative to the strain RRI/pBR322 used as the control and treated under the same conditions. This band has an apparent molecular weight of the order of 39±3 kDa, which is slightly less than the apparent molecular weight of the purified chitinase of *A. album* obtained in section 1.

Immunoblotting

The electrophoresis conditions described in the previous paragraph are maintained. The gel is not stained with Coomassie blue, but the proteins are transferred to a nitrocellulose filter according to the technique described by Towbin et al., 1979, Proc. Ntl. Acad. Sci. USA, 76, 4350–4354, and immunodetection is performed according to the protocol described in section 8.

The blot obtained shows that the additional protein has an apparent molecular weight of about 39±3 kDa, which is slightly less than that of the chitinase of *A. album* isolated in section 1. This protein, which is present in the strain RRI/pEMR682 and absent from the control strain, is recognized by antibodies directed against the chitinase of *A. album*.

Detection of chitinolytic activity in *E. coli*

The chitinolytic activity of the extracts of the strain RRI/pEMR682 and that of the control strain are measured by the radiochemical method of Molano et al., summarized in paragraph b1 of section 1. The results, which are collated in Table II below, show that the strain RRI/pEMR682 has chitinolytic activity, in contrast to the control strain.

TABLE II

Comparison of the chitinolytic activity of the strain RRI/pEMR682 and the control strain for a protein extract at OD = 1 which contains 10 µg of total proteins (amount measured by Bradford's method)

| | Chitinolytic activity (dpm/µg of protein) | |
|---|---|---|
| | Control strain | Strain RRI/pEMR682 |
| 1st experiment | 128 | 260 |
| 2nd experiment | 145 | 1150 |
| 3rd experiment | 130 | 410 |
| 4th experiment | 185 | 600 |
| 5th experiment | 195 | 564 |
| 6th experiment | 120 | 583 |

Section 10: Expression of the chitinase of *Aphanocladium album* in yeast (*Saccharomyces cerevisiae*) and secretion with the aid of the signal peptide of pheromone α a) Construction of plasmid pEMR698, a vector for the expression of the mature chitinase of *Aphanocladium album*:

Plasmid pEMR583 is described in European patent 0 273 800. In particular, it comprises a fragment of plasmid pBR322 carrying the origin of replication in *E. coli* and the ampicillin resistance gene, a fragment of plasmid 2µ which permits replication in yeast, and the genes complementing the auxotrophy of leucine, as well as an IL-8 expression cassette containing a Gal7-ADH2hybrid promoter, the signal peptide of pheromone α, a sequence coding for mature IL-8 and a terminator.

Plasmid pEMR583 is hydrolyzed with the enzymes HindIII and BamHI and the large HindIII-BamHI fragment is purified; this fragment carries the expression system necessary in yeast. It is assembled and ligated with the AccI-BamHI fragment derived from plasmid pEMR680 described in section 9 and with a synthetic HindIII-AccI oligonucleotide of the following sequence (Nt2), which reconstitutes the 3' sequence of the prepro-region of pheromone α of *S. cerevisiae* missing from the large HindIII-BamHI fragment derived from plasmid pEMR583, and the 5' end of the mature chitinase of *A. album* missing from the AccI-BamHI fragment:

(Nt2)(SEQ ID NO: 23)
(HindIII)
AGC TTG GAT AAA AGA GGT AGT GGT TTT GCA AAT GCC GT
    AC CTA TTT TCT CCA TCA CCA AAA CGT TTA CGG CAG A
                                                                                                          (AccI)

The ligation mixture was used to transform the strain *E. coli* RRI. Plasmid pEMR698 is obtained.

b) Transformation of the yeast strain EMY761 by plasmid pEMR698, with selection for the prototrophy of leucine The strain EMY761 is a Mat α, leu2, ura3, his3 and gal yeast strain which is derived from the strain GRF18, well known to those skilled in the art (Gerry Fink, MIT, USA), by successive crosses of this strain with a ura3 strain obtained from the strain FL100 (deposited in the ATCC under no. 28 383) and with the strain 20B12 (Mat α, trp1, pep4) described by E. W. Jones, 1987, Genetics, 85, 23. This strain can be obtained by plasmid curing of the strain deposited in the CNCM on December 27, 1990 under no. I 1022.

The transformation technique used is a variant of that described by Beggs et al. (Beggs et al., (1978), Nature, 275, 104–109). It consists in subjecting the yeasts to a protoplastization treatment in the presence of an osmotic stabilizer, namely sorbitol at a concentration of 1M.

The precise transformation protocol is indicated in detail below:

a) 200 ml of liquid YPG medium (cf. Table III below) are inoculated with about $5 \times 10^6$ cells of a culture in the stationary phase, and the culture inoculated in this way is shaken overnight at 30° C.

b) When the culture reaches about $10^7$ cells per milliliter, the cells are centrifuged at 4000 rpm for 5 min and the residue is washed with 1M sorbitol.

c) The cells are suspended in 5 ml of 1M sorbitol solution containing 25 mM EDTA and 50 mM dithiothreitol, and incubated for 10 min at 30° C.

d) The cells are washed once with 10 ml of 1M sorbitol and suspended in 20 ml of sorbitol. Zymolyase-100T (a preparation obtained by partial purification of *Arthobacter luteus* culture supernatant on an affinity column and containing β-1,3-glucan-laminaripentahydrolase, marketed by SEYKAGAKU KOGYO Co. Ltd) is added to a final concentration of 20 µg/ml and the suspension is incubated at room temperature for about 15 min.

e) The cells are resuspended in 20 ml of a sorbitol-containing medium called YPG sorbitol medium (cf. Table III below) and incubated for 20 min at 30° C., with gentle shaking.

f) The suspension is centrifuged for 3 min at 2500 rpm.

g) The cells are resuspended in 9 ml of transformation buffer (sorbitol 1M, Tris-HCl pH 7.5 10 mM and $CaCl_2$ 10 mM).

h) 0.1 ml of cells and 5 µl of DNA solution (about 5 µg) of plasmid pEMR698 are added and the suspension obtained is left for 10 to 15 min at room temperature.

i) 1 ml of the following solution is added: polyethylene glycol PEG 4000 20%, Tris-HCl pH 7.5 10 mM and $CaCl_2$ 10 mM.

j) 0.1 ml of the suspension obtained in i) is poured into a tube containing leucine-free solid regeneration medium (cf. Table III below) which has been melted beforehand and kept liquid at about 45° C. The suspension is poured into a Petri dish containing a solidified layer of 15 ml of leucine-free solid regeneration medium.

k) Step j) is repeated with the remainder of the cell suspension obtained in i).

The transformants start to appear after 3 days.

The retained transformant is called EMY761-/pEMR698.

TABLE III

Principal media used in sections 10 and 11 —leucine-free solid medium 6.7 g of yeast nitrogen base without amino acids (from DIFCO)
    20 mg of adenine
    20 mg of uracil
    20 mg of l-tryptophan
    20 mg of l-histidine
    20 mg of l-arginine
    20 mg of l-methionine
    30 mg of l-tyrosine
    30 mg of l-isoleucine
    30 mg of l-lysine
    50 mg of l-phenylalanine
    100 mg of l-glutamic acid
    150 mg of l-valine
    400 mg of l-leucine
    20 g of glucose
    20 g of agar Mix all the ingredients in distilled water. Make up to a final volume of 1 l with distilled water. Autoclave for 15 min at 120° C. After autoclaving, add 200 mg of l-threonine and 100 mg of l-aspartic acid.

leucine-free solid regeneration medium

Use the formulation of the leucine-free solid medium, but mix 30 g of agar instead of 20 and add 182 g of sorbitol to the mixture.

leucine-free liquid medium

Use the formulation of the leucine-free solid medium, but omit the agar. Autoclave for 15 min at 120° C. After autoclaving, add 200 mg of l-threonine and 100 mg of l-aspartic acid.

liquid YP medium 10 g of yeast extract (Bacto-yeast extract from DIFCO)

20 g of peptone (Bacto-peptone from DIFCO)

Mix the ingredients in distilled water. Make up to a final volume of 1 l with distilled water. Autoclave for 15 min at 120° C.

liquid YPG medium

Use the formulation of the liquid YP medium and, after autoclaving, add glucose to a concentration of 20 g/l.

YP ethanol/glycerol/galactose medium

Use the formulation of the liquid YP medium. After autoclaving, add 10 ml of 100% ethanol, 30 g of glycerol and 30 g of galactose.

c) Expression of the chitinase of *A. album* by the strain EMY761/pEMR698

The preliminary cultures are prepared in a medium of the following composition: liquid YP medium 1.4%, glucose 3%, histidine 50 μg/ml and uracil 50 μg/ml. After 24 h, the cultures are centrifuged and the residue is taken up in 40 ml of a medium of the following composition: liquid YP medium 1.4%, ethanol 1%, casamino acids 1%, uracil 100 μg/ml, glycerol 3% and galactose 1%.

d) Analysis of the proteins present in the culture medium

Preparation of the samples

After culture for 24 h, the cells cultivated in c) were centrifuged for 20 min and the supernatant was collected. 5 ml of 50% trichloroacetic acid containing 2 mg/ml of deoxycholate were added to 10 ml of supernatant.

The mixture was left at +4° C. for 30 min and then centrifuged for 30 min. The residue was taken up in about 1 ml of cold acetone (+4° C.) and centrifuged again for 30 min. After drying, the residue is taken up in about 20 μl of a so-called loading buffer consisting of Tris-HCl 0.125M pH 6.8, SDS 4%, bromophenol blue 0.002%, glycerol 20% and β-mercaptoethanol 10% (according to the protocol described by Laemmli (1970)). The residue is solubilized by boiling for 15 min and then neutralized by the addition of 10N sodium hydroxide.

Analysis of the proteins by electrophoresis in denaturing SDS gel is performed according to the method described in section 9 d).

The profile obtained shows an additional wide band which is present in the strain EMY761/pEMR698 and absent from the control strain (non-transformed strain EMY761). This band has a molecular weight of between 39 and 46 kDa. The width of this band probably results from different degrees of glycosylation of the protein, which possesses two potential N-glycosylation sites (cf. FIGS. 1(A) and 1(B)). Western blot shows that this protein is recognized by antibodies directed against the chitinase of *Aphanocladium album*.

e) Detection of chitinolytic activity in *Saccharomyces cerevisiae* culture supernatant The chitinolytic activity of extracts of culture supernatant of the strain EMY761/pEMR698 and the control strain is measured by Molano's radiochemical method (1977, Anal. Biochem., 83, 648–656) summarized in paragraph b1 of section 1.

The results, which are collated in Table IV below, show that the chitinolytic activity of the culture supernatant of the strain transformed by plasmid pEMR698 is greater than that of the culture supernatant of the control strain.

TABLE IV

Comparison of the chitinolytic activity of the yeast strain EMY761/pEMR698 and the control strain for an extract of culture supernatant, concentrated by diafiltration, which contains 10 μg of total proteins (amount measured according to Bradford's method), each value being the average of 4 independent measurements

| | Chitinolytic activity (dpm/μg of protein) | |
|---|---|---|
| | Control strain | Strain EMY761/pEMR698 |
| experiment 1 | 156 | 730 |
| experiment 2 | 270 | 560 |
| experiment 3 | 120 | 750 |

Section 11

Expression of the chitinase of *A. album* in yeast and secretion with the aid of its own signal peptide a) Construction of plasmid pEMR697, a vector for the expression of the prepro-chitinase of *Aphanocladium album*

Plasmid pEMR473 is described in European patent application 0 408 461. In particular, it comprises a fragment of plasmid pBR322 carrying the origin of replication in *E. coli* and the ampicillin resistance gene, a fragment of plasmid 2μ which permits replication in yeast, and the genes complementing the auxotrophy of leucine, as well as a cassette for the expression of the urate oxidase of *Aspergillus flavus*, containing a Ga17-ADH₂hybrid promoter, a sequence coding for the urate oxidase of *A. flavus* and a terminator.

Plasmid pEMR473 is hydrolyzed partially with ClaI and completely with BamHI. The purified large Bam- HI-ClaI fragment is the whole plasmid from which the gene coding for urate oxidase has been deleted. This fragment is ligated in the presence of the synthetic oligonucleotide of sequence (Nt3), which makes it possible to join the non-coding 3' end of the complementary DNA of urate oxidase, the 5' part of the prepro-sequence of the chitinase of *A. album* and the PstI-BamHI fragment of pEMR680, which carries the 3' part of the coding sequence of the chitinase of *A. album*. The ligation mixture is used to transform *E. coli* RRI. The resulting plasmid is pEMR697.

site at the 3' end, so as to reconstitute a BamHI site, and on the other hand at the 3' end with the oligonucleotide of sequence (Nt5) below, carrying a sticky site, compatible with the BamHI site, at the 5' end and a SacI site at the 3' end, so as to reconstitute a SacI site. The fragment obtained contains the coding sequence of the complementary DNA of the preprochitinase of *Aphanocladium album*, bordered by a BamHI site at the 5' end and a SacI site at the 3' end. These two sites will subsequently permit insertion with a promoter and a terminator.

The sequences of the oligonucleotides used are given (Nt3)(SEQ. ID NO: 24)
```
CGA TAT ACA CAA TGT TGA GCT TTG TCA AAA AGT CGA TCG CCT TGG
    T ATA TGT GTT ACA ACT CGA AAC AGT TTT TCA GCT AGC GGA ACC
TGG CGG CCC TGC A
ACC GCC GGG
``` b) Transformation of the yeast strain EMY761 by plasmid pEMR697, with selection for the prototrophy of leucine cf. section 10 b)

The transformant is called EMY761/pEMR697.

c) Culture of the strain EMY761/pEMR697 cf. section 10 c)

d) Analysis of the proteins present in the culture medium 25 cf. section 10 d)

e) Detection of chitinolytic activity in *Saccharomyces cerevisiae* cf. section 10 e)

The results are collated in Table V below.

below, the restriction sites being indicated in brackets:

(Nt4) (SEQ ID NO: 25)
(BamHI)
GATCCGCTAA CTGACAT
    GCGATT GACTGTAGC
            (ClaI)

(Nt5)(SEQ ID NO: 26)
(compatible with BamHI)
GATCGAACTG TACCGAGCT
    CTTGAC ATGGC
            (SacI)

TABLE V

Comparison of the chitinolytic activity of the yeast strain EMY761/pEMR697 and the control strain for an extract of culture supernatant which contains 10 μg of total proteins (amount measured according to Bradford's method)

| | Chitinolytic activity (dpm/μg of protein) | |
|---|---|---|
| | Control strain | Strain EMY761/pEMR697 |
| experiment 1 | 156 | 624 |
| experiment 2 | 270 | 2819 |
| experiment 3 | 120 | 350 |

The ligation is carried out with the aid of T4 DNA ligase.

Construction 2: Gene coding for the mature chitinase of *Aphanocladium album*, preceded by the signal peptide of a bean chitinase The complementary DNA carrying part of the coding sequence of the mature chitinase of *Aphanocladium album* was obtained from plasmid pEMR680, described in section 9, by partial digestion with the endonucleases AccI and BamHI. The resulting fragment of about 1100 base pairs, which contains the coding part of the mature chitinase of *A. album* except for the first 23 base pairs, is ligated on the one hand at the 5' end with the oligonucleotide of sequence (Nt6) below, and on the other hand at the 3' end with the oligonucleotide of sequence (Nt5). The oligonucleotide (Nt6) contains a BamHI site at the 5' end, the sequence coding for the signal peptide of a bean chitinase (Broglie K. E. et al., 1986, Proc. Ntl. Acad. Sci. USA, 83, 6820–6824), the first 23 base pairs missing from the mature chitinase of *A. album*, and an AccI site at the 3' end.

Section 12

Construction of two vectors for the expression of the chitinase of *Aphanocladium album* in plant cells a) Preparation of a gene coding for the mature chitinase of *A. album*, preceded by a signal peptide Construction 1: Gene coding for the prepro-chitinase of *A. album*

The complementary DNA carrying the coding sequence of the prepro-chitinase of *A. album* was obtained by cleavage of vector pEMR697, described in section 11, with the restriction enzymes ClaI and BamHI. The fragment obtained was purified by electrophoresis on low- melting agarose gel. This fragment carries the coding sequence of the complementary DNA of the prepro-chitinase of *Aphanocladium album*, the initiation ATG being preceded by an 11 bp fragment carrying the ClaI site. This fragment was ligated on the one hand at the 5' end with the oligonucleotide of sequence (Nt4) below, carrying a BamHI site at the 5' end and a ClaI The fragment obtained contains the coding sequence of the mature chitinase of *Aphanocladium album*, which is fused to the coding sequence of the signal peptide of a 5 bean chitinase, which in turn is bordered by a BamHI site at the 5' end and a SacI site at the 3' end.

The sequence of the oligonucleotide (Nt6) used is given below (SEQ ID NO:27), the restriction sites being indicated in brackets:

(Nt6)
(BamHI)
```
GATCCATGAA GAAGAATAGG ATGATGATGA TGATATGGAG CGTAGGAGTG GTGTGGATGC    60
    GTACTT CTTCTTATCC TACTACTACT ACTATACCTC GCATCCTCAC CACACCTACG
TGTTGTTGGT TGGAGGAAGC TACGGAGGTA GTGGTTTTGC AAATGCCGT              109
ACAACAACCA ACCTCCTTCG ATGCCTCCAT CACCAAAACG TTTACGGCAG A
                                                            (AccI)
```

Part of the sequence (Nt6) coding for the signal peptide of a bean chitinase (SEQ ID N0:29) as well as the deduced amino acid sequence of said signal peptide (SEQ ID NO:28), shown beneath the nucleotide sequence, are indicated below:

```
ATG AAG AAG AAT AGG ATG ATG ATG ATG ATA TGG AGC GTA GGA GTG GTG   48
Met Lys Lys Asn Arg Met Met Met Met Ile Trp Ser Val Gly Val Val
TGG ATG CTG TTG TTG GTT GGA GGA AGC TAC GGA                        81
Trp Met Leu Leu Leu Val Gly Gly Ser Tyr Gly
``` b) Preparation of the promoter sequence comprising the 35S promoter of cauliflower mosaic virus The HindIII-BamHI fragment of about 900 bp, containing the 35S promoter, is isolated from plasmid pBI121 (Clontech) by cleavage with the endonucleases HindIII and BamHI, followed by electrophoresis on agarose gel. This fragment is cleaved again with HindII. The fragment of about 410 bp, carrying the BamHI site, is treated with T4 DNA ligase in the presence of a HindIII linker (a synthetic sequence containing a HindIII site). After cleavage with the endonuclease HindIII and electrophoresis on agarose gel, the resulting HindIII-BamHI fragment (of about 420 bp) is isolated and purified.

c) Preparation of the terminator sequence comprising the terminator of the nopaline synthase (NOS) of *Agrobacterium tumefaciens*

A fragment of about 250 bp, containing the terminator of nopaline synthase, was isolated from plasmid pBI121 (Clontech) by cleavage with the restriction enzymes SacI and EcoRI, followed by electrophoresis on agarose gel.

Cloning into binary vector pBIN19

T4 DNA ligase was used to ligate the promoter sequence (cf. section 12 b)), the coding sequence of the complementary DNA of the chitinase of constructions 1 and 2, and the terminator sequence (cf. section 12 c)) into binary vector pBIN19 opened with the endonucleases HindIII and EcoRI. This vector carries two kanamycin resistance genes, one being capable of expression in bacteria and the other, located immediately upstream of the complete recombinant gene (cf. Bevan, 1984, Nucl. Ac. Res., 12, 8711–8721), being capable of transfer to plant cells. The kanamycin resistance gene will be used as a selection marker during the steps for transformation and analysis of the descendants of the transformed plants.

The vector obtained is called plasmid pBR61 if it contains construction 1 and plasmid pBR62 if it contains construction 2. The nucleotide sequence of the complete recombinant gene was verified by sequencing for each of plasmids pBR61 and pBR62. The coding sequence of this gene, bordered by the BamHI and SacI restriction sites, is shown in FIGS. 4(A) and 4(B) for plasmid pBR61 and in FIGS. 5(A) and 5(B) for plasmid pBR62. These plasmids are cloned into the strain *E. coli* JM109 (Stratagene).

Section 13

Transfer, into *Agrobacterium tumefaciens*, of plasmids pBR61 and pBR62 containing a gene coding for the chitinase of *Aphanocladium album* a) Transfer into *Agrobacterium tumefaciens*

This transfer is effected as described below by triparental conjugation between the strain *E. coli* JM109 (Sambrook et al., op. cit.), containing vector pBR61 or pBR62, and the strain *Agrobacterium tumefaciens* LBA4404 (Clontech) with the aid of the strain *E. coli* HB101, containing mobilizing plasmid pRK2013 (D. M. Figurski et al., 1979, Proc. Ntl. Acad. Sci. USA, 76, 1648–1652).

The strain *E. coli* JM109, containing plasmid pBR61 or pBR62, and a strain *E. coli* HB101 (Clontech), containing mobilizing plasmid pRK2013, are cultivated at 37° C. in Luria medium (Gibco) in the presence of 25 mg/l of kanamycin.

The strain *Agrobacterium tumefaciens* LBA4404 is cultivated at 28° C. in Luria medium (Gibco) in the presence of 100 mg/l of rifampicin (it is resistant to this antibiotic); 200 µl of each of the three cultures are mixed, plated out on gelose-containing Luria medium (Gibco) and incubated overnight at 28° C. The bacteria are then resuspended in 5 ml of Luria medium and aliquots are plated out on Petri dishes containing a minimum gelose medium (described in "Plant Molecular Biology Manual", Gelvin et al., Kluwer Academic Press, 1988) in the presence of 100 mg/l of rifampicin and 25 mg/l of kanamycin. Only those colonies of *Agrobacterium tumefaciens* which have integrated plasmid pBR61 or pBR62 grow under these conditions (the *E. coli* strains cannot grow under these conditions). Said colonies contain the recombinant gene of chitinase in a context which permits its replication.

The resistance of the selected colonies to both antibiotics is verified by subculture of the colonies on the same selection medium twice in succession. The presence of the recombinant gene of chitinase in *Agrobacterium tumefaciens* is verified by the Southern blot method on a total DNA preparation (lysis of the cells, purification of the DNA by extraction with a phenol/chloroform mixture according to the protocol described by Gelvin in the work cited above, cleavage of the purified DNA with restriction enzymes, electrophoresis on agarose gel, transfer to a membrane and hybridization according to the techniques well known to those skilled in the art).

b) Transfer into *Agrobacterium rhizogenes*

This transfer is effected in the same way as the transfer into *Agrobacterium tumefaciens* described in a), with the strain *Agrobacterium rhizoaenes* A4 described by GUERCHE et al., (1987), Mol. Gen. Genet., 206, 382.

Section 14: Production of transformed tobacco plants

The tobacco *Nicotiana tabacum*, cultivated in vitro, was infected with *Agrobacterium tumefaciens*, containing plasmid pBR61 or pBR62, according to the procedure of Horsch et al., which is well known to those skilled in the art (Horsch R. B. et al., 1985, Science, 227, 1229–1231) and the principal steps of which are explained below.

Discs of leaves of axenic plants of the tobacco *N. tabacum* (Wisconsin Havana 38 variety sensitive to pathogenic fungi) are incubated in a culture of *A. tumefaciens* containing plasmid pBR61 or pBR62. The discs, drained on Whatman paper, were transferred to culture media in Petri dishes so as to multiply the transformed cells to give calluses, and subsequently regenerated plants.

Section 15: Detection of the expression of the chitinase of A. album in the transformed tobacco calluses and plant leaves a) Preparation of the crude protein extracts of transformed tobacco The tissue fragments (calluses or plant leaves) were frozen in liquid nitrogen, reduced to powder and stored at −20° C. The powder was extracted at 4° C. in the presence of a 0.1M ammonium acetate buffer of pH 5.2 and centrifuged at 10,000 g. The total protein concentration was determined on the supernatants, hereafter called the crude protein extracts, according to Bradford's technique (Bradford M. M., 1976, Anal. Biochem., 72, 248-254).

b) Detection of the recombinant chitinase by immunoblotting (Western blot)

The crude protein extracts of different transformed calluses (or plant leaves) and non-transformed calluses (or plant leaves) (controls) are subjected to a Western blot, a technique well known to those skilled in the art and described in particular by H. Towbin et al., Proc. Ntl. Acad. Sci. USA, 76, 1979, 4350-4354, which comprises the following steps:

denaturation by heating at 100° for 10 min in a buffer, called a loading buffer, consisting of Tris- HCl 0.125M pH 6.8, SDS 4%, bromophenol blue 0.002%, glycerol 20% and β-mercaptoethanol 10% (according to the protocol described by Laemmli, U.K. Laemmli, Nature, 227, 1970, 680-685);
  electrophoretic separation of the different proteins contained in the solubilizate according to the protocol described by Laemmli (op. cit.);
  electrotransfer of said proteins contained in the gel to a PVDF membrane (according to the technique of H. Towbin et al., Proc. Natl. Acad. Sci. USA, 76, 1979, 4350-4354).

Immunodetection is effected according to a protocol which comprises the following steps:

saturation of the PVDF membrane to which the proteins have been transferred by incubation for at least 2 h at 37° C. in a 3% solution of gelatin;
  3 washes in phosphate buffered saline containing 0.05% of Tween 20 detergent;
  incubation (for 1 h at 37° C.) in the presence of the previously prepared immune serum (containing the polyclonal antibodies recognizing the recombinant protein) diluted to 1/10,000 in phosphate buffered saline;
  3 washes in phosphate buffered saline containing 0.05% of Tween 20 detergent.

The antigen-antibody complex is then developed with the aid of a streptavidin-biotin system conjugated with alkaline phosphatase using the RPN 23 kit from Amersham ("Blotting detection kit") in accordance with the manufacturer's instructions.

The blot obtained shows the presence of a protein with an apparent molecular weight of about 41±3 kDa for the tobacco calluses and plant leaves transformed by each of plasmids pBR61 and pBR62, which is absent from the control calluses and plant leaves. This protein has the same apparent molecular weight as the purified chitinase of A. album obtained in section 1.

c) Detection of the chitinolytic activity of the recombinant chitinase

The chitinolytic activity of the 5 crude protein extracts of tobacco calluses and plant leaves transformed by each of plasmids pBR61 and pBR62 and 5 crude protein extracts of non-transformed tobacco calluses and plant leaves is measured according to the radiochemical method of Molano et al., described in section 1 b1. In view of the endogenous chitinolytic activity, a simple means of showing the chitinolytic activity of the recombinant chitinase is specifically to inactivate the latter with antibodies and observe the drop in total chitinolytic activity of the extracts.

10 μl of these crude extracts are brought into contact, for 5 min at room temperature, with 1 μl of the polyclonal antibodies directed against the chitinase of A. album (prepared in section 1 c)). The chitinolytic activity of these crude extract/antibodies mixtures is also measured by the radiochemical method of Molano et al. (section 1 b)).

The chitinolytic activity of the crude protein extracts of tobacco calluses and plant leaves transformed by each of plasmids pBR61 and pBR62 is significantly higher than that of the extracts of the control calluses and plant leaves. After incubation in the presence of antibodies against the chitinase of A. album, the activity of the extracts of tobacco calluses and plant leaves transformed by each of plasmids pBR61 and pBR62 decreases, whereas that of the extracts of the control calluses and plant leaves is not affected.

The recombinant chitinase of A. album expressed in tobacco therefore possesses chitinolytic activity.

d) Purification of the recombinant chitinase and determination of its amino-terminal sequence d1) Purification of the recombinant chitinase The recombinant protein was purified from the crude protein extracts of tobacco plant leaves transformed by each of plasmids pBR61 and pBR62 by precipitation with ammonium sulphate and then liquid chromatography according to Pharmacias's FPLC technique on a cation exchange column based on synthetic polymer on a crosslinked agarose according to the protocol described below:

Protocol for the purification of the recombinant chitinase step 1

The protein extract is precipitated with ammonium sulphate (60% saturation). The proteins which have precipitated are recovered by centrifugation (15,000 g for 30 min) and subsequently solubilized in a buffer solution (100 mM ammonium acetate, pH 5.2) and dialyzed overnight at 4° C. against a 100mM ammonium acetate buffer solution of pH 5.2.

Immediately before proceeding, the concentration of the buffer solution of the protein extract is brought to 10mM by passage through ready-to-use minicolumns (Pharmacia PD10).

step 2

The protein extract is then purified by chromatography on an ion exchange column based on synthetic polymer (Mono S column from Pharmacia) according to Pharmacia's FPLC technique.

The extract is deposited on the Mono S column equilibrated with a 10mM ammonium acetate buffer solution of pH 5.2. The proteins retained on the column are eluted by a linear gradient of 10 to 500 mM ammonium acetate.

At each step the chitinase is identified by its molecular weight (electrophoresis on a polyacrylamide gel in the presence of SDS-developing with silver), its immunoblot (cf. section 8b), and its activity which is measured by the radiochemical method described in section 1.b1.

d2) Determination test of the amino-terminal sequence of the recombinant chitinase After purification of the recombinant chitinase according to the protocol described above, sequencing of the amino-terminal end was carried out. The samples to be treated are placed on the surface of a PVDF (Polyvinylidenedifluoride) filter by electrotransfer according to the method described by H. Towbin et al., Proc. Natl.Acad. Sci. USA (1979), 4350–4354 after electrophoresis on a polyacrylamide gel in the presence of SDS. The filter is introduced into a protein sequencer (model 470 A, marketed by Applied Biosystems, USA) equipped with a chromatograph (model 430 from Applied Biosystems), which continuously analyzes the phenylthiohydantoic derivatives formed after each degradation cycle.

The following amino-terminal sequence (amino acids 1–12 of SEQ ID NO:1) is obtained for the recombinant protein obtained from the tobacco leaves transformed by each of plasmids pBR61 and pBR62:

```
Gly Ser Gly Phe Ala Asn Ala Val Tyr Phe Thr Asn
 1           5                   10
```

Cleavage of the signal peptide therefore occurs at the expected site.

Section 16: Production of transformed colza plants

Transformation is effected according to the protocol of P. Guerche et al. (P. Guerche et al., 1987, Mol. Gen. Genet., 206, 382). The different culture media are those described by Pelletier et al. (Pelletier et al., 1983,Mol. Gen. Genet., 191–244). Their composition will be explained below (Table VI).

a) Production of transformed roots

Stem segments are taken from the apical end of colza plants (*Brassica napus*: spring varieties Brutor, Westar and winter varieties) of about 1 m in height. These segments are sterilized on the surface, rinsed in sterile water, cut into segments of about 1.5 cm in length and placed in a tube containing medium A.

The end of this segment is inoculated by the deposition of a suspension of the *Agrobacterium rhizogenes* strain containing plasmid pBR61 or pBR62.

Transformed roots appear on the stem segment after 1 to 2 weeks; they are removed and placed on medium B containing gelose (15 g/l) and complemented with 500 μg of cefotaxim/ml.

b) Regeneration of transformed plants

Root fragments are incubated for 15 days on medium D containing 3 mg/l of 2,4-dichlorophenoxyacetic acid and are then placed on RCC medium for inducing buds. Rooted plants are then obtained by transfer of the buds to media F and G (Table VI below).

TABLE VI

Composition of the different media used to obtain transformed colza plants

| Composition (mg/l) | A | B | RCC | F | G |
|---|---|---|---|---|---|
| $NH_4NO_3$ | 1650 | | 1650 | 1650 | 825 |
| $KNO_3$ | 1900 | 2500 | 1900 | 1900 | 950 |
| $(NH_4)_2SO_4$ | | 134 | | | |
| $NaH_2PO_4$ | | 150 | | | |
| $KH_2PO_4$ | 170 | | 170 | 170 | 85 |
| $CaCl_2.2H_2O$ | 440 | 750 | 440 | 440 | 220 |
| $MgSO_4.7H_2O$ | 370 | 250 | 370 | 370 | 185 |
| $H_3BO_3$ | 12.4 | 3 | 12.4 | 6.2 | 6.2 |
| $MnSO_4.4H_2O$ | 33.6 | 10 | 33.6 | 22.3 | 22.3 |
| $ZnSO_4.7H_2O$ | 21 | 2 | 21 | 8.6 | 8.6 |
| KI | 1.66 | 0.75 | 1.66 | 0.83 | 0.83 |
| $Na_2MoO_4.2H_2O$ | 0.5 | 0.25 | 0.5 | 0.25 | 0.25 |
| $CuSO_4.5H_2O$ | 0.05 | 0.025 | 0.05 | 0.25 | 0.25 |
| $CoCl_2.6H_2O$ | 0.05 | 0.025 | 0.05 | 0.25 | 0.25 |
| $FeSO_4.7H_2O$ | 22.24 | 27.8 | 27.8 | 27.8 | 22.24 |
| $Na_2EDTA$ | 29.84 | 37.3 | 37.3 | 37.3 | 29.84 |
| Inositol | 100 | 100 | 100 | 100 | 100 |
| Nicotinic acid | 0.5 | 1 | 0.5 | 1 | 0.5 |
| Pyroxidine.HCl | 0.5 | 1 | 0.5 | 1 | 0.5 |
| Thiamine | | 10 | | 10 | |
| Glycine | 2 | | 2 | | 2 |
| Glucose | 10,000 | 20,000 | | | 10,000 |
| Sucrose | 10,000 | | 10,000 | 10,000 | |
| D-Mannitol | | 70,000 | 10,000 | | |
| NAA | | 1 | 1 | 0.1 | 0.1 |
| BAP | | 1 | 0.5 | 0.5 | |
| 2,4-D | | 0.25 | | | |
| Adenine sulfate | | | | | |
| IPA | | | 0.5 | | |
| $GA_3$ | | | 0.02 | | |
| Tween 80 | | 10 | | | |
| Agar | 8000 | | 8000 | 8000 | 8000 |
| pH | 5.8 | 5.8 | 5.8 | 5.8 | 5.8 |
| Gentamycin (sulfate) | 10 | | | | |

NAA = naphthaleneacetic acid
BAP = 6-benzylaminopurine
2,4-D = 2,4-dichlorophenoxyacetic acid
IPA = $N^6$-($\Delta^2$-isopentenyl)adenine
$GA_3$ = gibberellic acid
EDTA = ethylenediaminetetraacetic acid Section 17: Detection of the expression of the chitinase of *A. album* in transformed colza roots a) Preparation of the crude protein extracts of transformed colza roots The extracts are prepared as indicated in section 15 a).

b) Detection of the recombinant chitinase by immunoblotting (Western blot)

The protocol adopted is that described previously in section 15 b).

The blot obtained shows a protein with an apparent molecular weight of about 41±3 kDa, which is present in the roots transformed by plasmid pBR61 or plasmid pBR62 and absent from the extracts of non- transformed roots used as the control. This protein has the same apparent molecular weight as the purified natural chitinase of *A. album* obtained in section 1.

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 389 amino acids (B) TYPE: amino acid
(D) TOPOLOGY: linear (ii) MOLECULE TYPE: protein (vii) IMMEDIATE SOURCE:
(B) CLONE: protein having endochitinase activity (xi) SEQUENCE DESCRIPTION: SEQ ID NO:1:

```
Gly Ser Gly Phe Ala Asn Ala Val Tyr Phe Thr Asn Trp Gly Ile Tyr
 1               5                  10                  15
Gly Arg Asn Phe Gln Pro Ala Asp Leu Pro Ala Ser Glu Ile Thr His
                20                  25                  30
Val Leu Tyr Ser Phe Met Asn Val Arg Ala Asp Gly Thr Ile Phe Ser
            35                  40                  45
Gly Asp Thr Tyr Ala Asp Tyr Glu Lys His Tyr Ala Gly Asp Ser Trp
50                      55                  60
Asn Asp Val Gly Thr Asn Ala Tyr Gly Cys Val Lys Gln Leu Tyr Leu
65                  70                  75                  80
Leu Lys Lys Gln Asn Arg Asn Met Lys Val Met Leu Ser Ile Gly Gly
                85                  90                  95
Trp Thr Trp Ser Thr Asn Phe Pro Ala Ala Ala Ser Ser Ala Ala Thr
               100                 105                 110
Arg Lys Thr Phe Ala Gln Ser Ala Val Gly Phe Met Lys Asp Trp Gly
            115                 120                 125
Phe Asp Gly Ile Asp Ile Trp Glu Tyr Pro Ala Asp Ala Thr Gln
130                     135                 140
Ala Gln Asn Met Val Leu Leu Leu Gln Ala Val Arg Ser Glu Leu Asp
145                     150                 155                 160
Ser Tyr Ala Ala Gln Tyr Ala Lys Gly His His Phe Leu Leu Ser Ile
                165                 170                 175
Ala Ala Pro Ala Gly Pro Asp Asn Tyr Asn Lys Leu Lys Phe Ala Glu
            180                 185                 190
Leu Gly Lys Val Leu Asp Tyr Ile Asn Leu Met Ala Tyr Asp Tyr Ala
            195                 200                 205
Gly Ser Trp Ser Asn Tyr Thr Gly His Asp Ala Asn Ile Tyr Ala Asn
210                     215                 220
Pro Gln Asn Pro Asn Ala Thr Pro Tyr Asn Thr Asp Asp Ala Val Gln
225                 230                     235                 240
Ala Tyr Ile Asn Gly Gly Val Pro Ala Asn Lys Ile Val Leu Gly Met
                245                 250                 255
Pro Ile Tyr Gly Arg Ser Phe Gln Gln Thr Glu Gly Ile Gly Lys Pro
            260                 265                 270
Tyr Asn Gly Ile Gly Ser Gly Ser Trp Glu Asn Gly Ile Trp Asp Tyr
            275                 280                 285
Lys Ala Leu Pro Lys Ala Gly Ala Thr Val Lys Cys Asp Asp Thr Ala
290                     295                 300
Lys Gly Cys Tyr Ser Tyr Asp Pro Ser Thr Lys Glu Leu Ile Ser Phe
305                     310                 315                 320
Asp Thr Pro Ala Met Ile Ser Thr Lys Val Ser Trp Leu Lys Gly Lys
                325                 330                 335
Gly Leu Gly Gly Ser Met Phe Trp Glu Ala Ser Ala Asp Lys Lys Gly
            340                 345                 350
Ser Asp Ser Leu Ile Ser Thr Ser His Gln Gly Leu Gly Ser Gln Asp
            355                 360                 365
Ser Thr Gln Asn Tyr Leu Asp Tyr Pro Asn Ser Lys Tyr Asp Asn Ile
370                     375                 380
```

```
Lys  Lys  Gly  Met  Asn
385
```

( 2 ) INFORMATION FOR SEQ ID NO:2:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: signal peptide of preproendothiapepsin ( x i ) SEQUENCE DESCRIPTION: SEQ ID NO:2:

```
Met  Ser  Ser  Pro  Leu  Lys  Asn  Ala  Leu  Val  Thr  Ala  Met  Leu  Ala  Gly
1              5                   10                       15

Gly  Ala  Leu  Ser  Ser  Pro  Thr  Lys  Gln  His  Val  Gly  Ile  Pro  Val  Asn
               20                  25                       30

Ala  Ser  Pro  Glu  Val  Gly  Pro  Gly  Lys  Tyr  Ser  Phe  Lys  Gln  Val  Arg
          35                  40                       45

Asn  Pro  Asn  Tyr  Lys  Phe  Asn  Gly  Pro  Leu  Ser  Val  Lys  Lys  Thr  Tyr
     50                  55                       60

Leu  Lys  Tyr  Gly  Val  Pro  Ile  Pro  Ala  Trp  Leu  Glu  Asp  Ala  Val  Gln
65                  70                       75                            80

Asn  Ser  Thr  Ser  Gly  Leu  Ala  Glu  Arg
                    85
```

( 2 ) INFORMATION FOR SEQ ID NO:3:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: signal peptide ( x i ) SEQUENCE DESCRIPTION: SEQ ID NO:3:

```
Met  Arg  Arg  Thr  Ser  Lys  Leu  Thr  Thr  Phe  Ser  Leu  Leu  Phe  Ser  Leu
1              5                   10                       15

Val  Leu  Leu  Ser  Ala  Ala  Leu  Ala
               20
```

( 2 ) INFORMATION FOR SEQ ID NO:4:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: signal peptide ( x i ) SEQUENCE DESCRIPTION: SEQ ID NO:4:

```
Met  Leu  Ser  Phe  Val  Lys  Lys  Ser  Ile  Ala  Leu  Val  Ala  Ala  Leu  Gln
1              5                   10                       15

Ala  Val  Thr  Ala  Leu  Ala
               20
```

( 2 ) INFORMATION FOR SEQ ID NO:5:

( i ) SEQUENCE CHARACTERISTICS:

( A ) LENGTH: 12 amino acids
( B ) TYPE: amino acid
( D ) TOPOLOGY: linear ( i i ) MOLECULE TYPE: peptide ( x i ) SEQUENCE DESCRIPTION: SEQ ID NO:5:

Thr Pro Ile Ser Ser Glu Ala Gly Val Glu Lys Arg
1               5                   10

( 2 ) INFORMATION FOR SEQ ID NO:6:

( i ) SEQUENCE CHARACTERISTICS:
( A ) LENGTH: 1167 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: sequence coding for SEQ ID NO: 1

( x i ) SEQUENCE DESCRIPTION: SEQ ID NO:6:

| | | | | | |
|---|---|---|---|---|---|
| GGTAGTGGTT | TTGCAAATGC | CGTCTACTTC | ACCAACTGGG | GCATTTATGG | CCGCAACTTC | 60 |
| CAGCCTGCCG | ACCTTCCTGC | CTCGGAGATT | ACTCACGTAC | TCTACTCCTT | CATGAATGTC | 120 |
| CGCGCAGATG | GCACCATCTT | TTCCGGTGAT | ACCTATGCCG | ACTACGAGAA | GCACTACGCT | 180 |
| GGTGACTCTT | GGAACGATGT | GGGCACGAAC | GCTTACGGTT | GTGTTAAGCA | ACTTTATCTT | 240 |
| CTCAAGAAGC | AGAACCGCAA | CATGAAGGTG | ATGCTGTCGA | TTGGTGGTTG | GACATGGTCT | 300 |
| ACCAACTTCC | CCGCTGCCGC | CAGCTCGGCT | GCTACCCGAA | AGACTTTTGC | TCAGTCTGCT | 360 |
| GTTGGCTTCA | TGAAGGACTG | GGGTTTCGAC | GGTATTGATA | TCGACTGGGA | GTACCCCGCC | 420 |
| GATGCCACTC | AGGCTCAGAA | TATGGTTCTC | TTGCTACAGG | CTGTCCGCAG | TGAGCTCGAC | 480 |
| TCCTACGCTG | CCCAGTACGC | CAAGGGTCAC | CACTTCCTGC | TTTCAATTGC | CGCCCCTGCT | 540 |
| GGACCTGACA | ATTATAACAA | GCTGAAGTTT | GCTGAGCTTG | GCAAGGTTCT | CGATTACATT | 600 |
| AACCTCATGG | CTTACGATTA | CGCTGGATCT | TGGAGCAACT | ACACTGGCCA | CGATGCCAAC | 660 |
| ATATACGCAA | ACCCGCAGAA | CCCCAACGCC | ACCCCTTACA | ACACGGACGA | TGCTGTCCAG | 720 |
| GCCTATATCA | ACGGCGGCGT | CCCTGCCAAC | AAGATCGTCC | TTGGTATGCC | AATCTACGGC | 780 |
| CGATCCTTCC | AGCAAACCGA | GGGTATCGGT | AAGCCTTACA | ATGGTATTGG | CTCTGGTAGC | 840 |
| TGGGAGAACG | GTATCTGGGA | CTACAAGGCT | CTCCCCAAGG | CTGGTGCCAC | CGTCAAGTGC | 900 |
| GACGATACCG | CCAAGGGATG | CTACAGCTAC | GATCCAAGCA | CTAAGGAGCT | TATTTCTTTC | 960 |
| GATACGCCGG | CTATGATCAG | CACCAAAGTT | AGCTGGCTCA | AGGGCAAGGG | CCTTGGCGGC | 1020 |
| AGCATGTTCT | GGGAGGCTTC | TGCCGACAAG | AAGGGCTCGG | ACTCTCTTAT | TAGCACCAGC | 1080 |
| CACCAAGGTC | TCGGTAGCCA | GGACAGCACT | CAGAACTACC | TCGACTACCC | TAACTCCAAG | 1140 |
| TACGACAACA | TCAAGAAGGG | CATGAAC | | | | 1167 |

( 2 ) INFORMATION FOR SEQ ID NO:7:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: sequence coding for SEQ ID NO: 4

( x i ) SEQUENCE DESCRIPTION: SEQ ID NO:7:

```
ATGTTGAGCT TTGTCAAAAA GTCGATCGCC TTGGTGGCGG CCCTGCAGGC GGTCACTGCC      60

CTGGCC                                                                 66
```

( 2 ) INFORMATION FOR SEQ ID NO:8:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( i i ) MOLECULE TYPE: cDNA ( v i i ) IMMEDIATE SOURCE:
            ( B ) CLONE: sequence coding for SEQ ID NO: 5

( x i ) SEQUENCE DESCRIPTION: SEQ ID NO:8:

```
ACGCCAATCT CCAGTGAAGC TGGTGTTGAG AAGCGC                                36
```

( 2 ) INFORMATION FOR SEQ ID NO:9:

( i ) SEQUENCE CHARACTERISTICS:
            ( A ) LENGTH: 1405 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: sigpeptide
            ( B ) LOCATION: 97..198

( i x ) FEATURE:
            ( A ) NAME/KEY: matpeptide
            ( B ) LOCATION: 199..1365

( i x ) FEATURE:
            ( A ) NAME/KEY: CDS
            ( B ) LOCATION: 97..1365

( x i ) SEQUENCE DESCRIPTION: SEQ ID NO:9:

```
AGCAACTCAA TAGGTACAAG CCTAACAGCA TAGCTCCCTC TAGAGTCAGC ACGCCGAATC       60

AGTTGATTCT CTACAACCTT CTGTACCTCA ACTACT ATG TTG AGC TTT GTC AAA       114
                                       Met Leu Ser Phe Val Lys
                                       -34                 -30

AAG TCG ATC GCC TTG GTG GCG GCC CTG CAG GCG GTC ACT GCC CTG GCC       162
Lys Ser Ile Ala Leu Val Ala Ala Leu Gln Ala Val Thr Ala Leu Ala
        -25             -20                     -15

ACG CCA ATC TCC AGT GAA GCT GGT GTT GAG AAG CGC GGT AGT GGT TTT       210
Thr Pro Ile Ser Ser Glu Ala Gly Val Glu Lys Arg Gly Ser Gly Phe
        -10                 -5                   1

GCA AAT GCC GTC TAC TTC ACC AAC TGG GGC ATT TAT GGC CGC AAC TTC       258
Ala Asn Ala Val Tyr Phe Thr Asn Trp Gly Ile Tyr Gly Arg Asn Phe
 5               10                 15                  20

CAG CCT GCC GAC CTT CCT GCC TCG GAG ATT ACT CAC GTA CTC TAC TCC       306
Gln Pro Ala Asp Leu Pro Ala Ser Glu Ile Thr His Val Leu Tyr Ser
                25              30                  35

TTC ATG AAT GTC CGC GCA GAT GGC ACC ATC TTT TCC GGT GAT ACC TAT       354
Phe Met Asn Val Arg Ala Asp Gly Thr Ile Phe Ser Gly Asp Thr Tyr
            40              45                  50

GCC GAC TAC GAG AAG CAC TAC GCT GGT GAC TCT TGG AAC GAT GTG GGC       402
Ala Asp Tyr Glu Lys His Tyr Ala Gly Asp Ser Trp Asn Asp Val Gly
        55              60                  65

ACG AAC GCT TAC GGT TGT GTT AAG CAA CTT TAT CTT CTC AAG AAG CAG       450
Thr Asn Ala Tyr Gly Cys Val Lys Gln Leu Tyr Leu Leu Lys Lys Gln
    70              75                  80
```

```
AAC  CGC  AAC  ATG  AAG  GTG  ATG  CTG  TCG  ATT  GGT  GGT  TGG  ACA  TGG  TCT       498
Asn  Arg  Asn  Met  Lys  Val  Met  Leu  Ser  Ile  Gly  Gly  Trp  Thr  Trp  Ser
85             90                       95                      100

ACC  AAC  TTC  CCC  GCT  GCC  GCC  AGC  TCG  GCT  GCT  ACC  CGA  AAG  ACT  TTT       546
Thr  Asn  Phe  Pro  Ala  Ala  Ala  Ser  Ser  Ala  Ala  Thr  Arg  Lys  Thr  Phe
               105                      110                     115

GCT  CAG  TCT  GCT  GTT  GGC  TTC  ATG  AAG  GAC  TGG  GGT  TTC  GAC  GGT  ATT       594
Ala  Gln  Ser  Ala  Val  Gly  Phe  Met  Lys  Asp  Trp  Gly  Phe  Asp  Gly  Ile
               120                      125                     130

GAT  ATC  GAC  TGG  GAG  TAC  CCC  GCC  GAT  GCC  ACT  CAG  GCT  CAG  AAT  ATG       642
Asp  Ile  Asp  Trp  Glu  Tyr  Pro  Ala  Asp  Ala  Thr  Gln  Ala  Gln  Asn  Met
               135                      140                     145

GTT  CTC  TTG  CTA  CAG  GCT  GTC  CGC  AGT  GAG  CTC  GAC  TCC  TAC  GCT  GCC       690
Val  Leu  Leu  Leu  Gln  Ala  Val  Arg  Ser  Glu  Leu  Asp  Ser  Tyr  Ala  Ala
     150                      155                      160

CAG  TAC  GCC  AAG  GGT  CAC  CAC  TTC  CTG  CTT  TCA  ATT  GCC  GCC  CCT  GCT       738
Gln  Tyr  Ala  Lys  Gly  His  His  Phe  Leu  Leu  Ser  Ile  Ala  Ala  Pro  Ala
165                      170                      175                     180

GGA  CCT  GAC  AAT  TAT  AAC  AAG  CTG  AAG  TTT  GCT  GAG  CTT  GGC  AAG  GTT       786
Gly  Pro  Asp  Asn  Tyr  Asn  Lys  Leu  Lys  Phe  Ala  Glu  Leu  Gly  Lys  Val
                    185                      190                     195

CTC  GAT  TAC  ATT  AAC  CTC  ATG  GCT  TAC  GAT  TAC  GCT  GGA  TCT  TGG  AGC       834
Leu  Asp  Tyr  Ile  Asn  Leu  Met  Ala  Tyr  Asp  Tyr  Ala  Gly  Ser  Trp  Ser
               200                      205                     210

AAC  TAC  ACT  GGC  CAC  GAT  GCC  AAC  ATA  TAC  GCA  AAC  CCG  CAG  AAC  CCC       882
Asn  Tyr  Thr  Gly  His  Asp  Ala  Asn  Ile  Tyr  Ala  Asn  Pro  Gln  Asn  Pro
               215                      220                     225

AAC  GCC  ACC  CCT  TAC  AAC  ACG  GAC  GAT  GCT  GTC  CAG  GCC  TAT  ATC  AAC       930
Asn  Ala  Thr  Pro  Tyr  Asn  Thr  Asp  Asp  Ala  Val  Gln  Ala  Tyr  Ile  Asn
     230                      235                      240

GGC  GGC  GTC  CCT  GCC  AAC  AAG  ATC  GTC  CTT  GGT  ATG  CCA  ATC  TAC  GGC       978
Gly  Gly  Val  Pro  Ala  Asn  Lys  Ile  Val  Leu  Gly  Met  Pro  Ile  Tyr  Gly
245                      250                      255                     260

CGA  TCC  TTC  CAG  CAA  ACC  GAG  GGT  ATC  GGT  AAG  CCT  TAC  AAT  GGT  ATT      1026
Arg  Ser  Phe  Gln  Gln  Thr  Glu  Gly  Ile  Gly  Lys  Pro  Tyr  Asn  Gly  Ile
               265                      270                     275

GGC  TCT  GGT  AGC  TGG  GAG  AAC  GGT  ATC  TGG  GAC  TAC  AAG  GCT  CTC  CCC      1074
Gly  Ser  Gly  Ser  Trp  Glu  Asn  Gly  Ile  Trp  Asp  Tyr  Lys  Ala  Leu  Pro
               280                      285                     290

AAG  GCT  GGT  GCC  ACC  GTC  AAG  TGC  GAC  GAT  ACC  GCC  AAG  GGA  TGC  TAC      1122
Lys  Ala  Gly  Ala  Thr  Val  Lys  Cys  Asp  Asp  Thr  Ala  Lys  Gly  Cys  Tyr
          295                      300                      305

AGC  TAC  GAT  CCA  AGC  ACT  AAG  GAG  CTT  ATT  TCT  TTC  GAT  ACG  CCG  GCT      1170
Ser  Tyr  Asp  Pro  Ser  Thr  Lys  Glu  Leu  Ile  Ser  Phe  Asp  Thr  Pro  Ala
     310                      315                      320

ATG  ATC  AGC  ACC  AAA  GTT  AGC  TGG  CTC  AAG  GGC  AAG  GGC  CTT  GGC  GGC      1218
Met  Ile  Ser  Thr  Lys  Val  Ser  Trp  Leu  Lys  Gly  Lys  Gly  Leu  Gly  Gly
325                      330                      335                     340

AGC  ATG  TTC  TGG  GAG  GCT  TCT  GCC  GAC  AAG  AAG  GGC  TCG  GAC  TCT  CTT      1266
Ser  Met  Phe  Trp  Glu  Ala  Ser  Ala  Asp  Lys  Lys  Gly  Ser  Asp  Ser  Leu
               345                      350                     355

ATT  AGC  ACC  AGC  CAC  CAA  GGT  CTC  GGT  AGC  CAG  GAC  AGC  ACT  CAG  AAC      1314
Ile  Ser  Thr  Ser  His  Gln  Gly  Leu  Gly  Ser  Gln  Asp  Ser  Thr  Gln  Asn
               360                      365                     370

TAC  CTC  GAC  TAC  CCT  AAC  TCC  AAG  TAC  GAC  AAC  ATC  AAG  AAG  GGC  ATG      1362
Tyr  Leu  Asp  Tyr  Pro  Asn  Ser  Lys  Tyr  Asp  Asn  Ile  Lys  Lys  Gly  Met
          375                      380                      385

AAC  TAAGCAGTCG  GTGTTTGCAT  AGCTTGATTG  ATGCTCGAGG                                  1405
Asn ( 2 ) INFORMATION FOR SEQ ID NO:10:
```

(i) SEQUENCE CHARACTERISTICS:
    (A) LENGTH: 423 amino acids
    (B) TYPE: amino acid
    (D) TOPOLOGY: linear (ii) MOLECULE TYPE: protein (xi) SEQUENCE DESCRIPTION: SEQ ID NO:10:

```
Met     Leu     Ser     Phe     Val     Lys     Lys     Ser     Ile     Ala     Leu     Val     Ala     Ala     Leu     Gln
-34             -30                                     -25                                     -20

Ala     Val     Thr     Ala     Leu     Ala     Thr     Pro     Ile     Ser     Ser     Glu     Ala     Gly     Val     Glu
                        -15                             -10                                             -5

Lys     Arg     Gly     Ser     Gly     Phe     Ala     Asn     Ala     Val     Tyr     Phe     Thr     Asn     Trp     Gly
                1                       5                                       10

Ile     Tyr     Gly     Arg     Asn     Phe     Gln     Pro     Ala     Asp     Leu     Pro     Ala     Ser     Glu     Ile
15                              20                                      25                                              30

Thr     His     Val     Leu     Tyr     Ser     Phe     Met     Asn     Val     Arg     Ala     Asp     Gly     Thr     Ile
                                35                                      40                                              45

Phe     Ser     Gly     Asp     Thr     Tyr     Ala     Asp     Tyr     Glu     Lys     His     Tyr     Ala     Gly     Asp
                        50                              55                                      60

Ser     Trp     Asn     Asp     Val     Gly     Thr     Asn     Ala     Tyr     Gly     Cys     Val     Lys     Gln     Leu
                65                              70                                      75

Tyr     Leu     Leu     Lys     Lys     Gln     Asn     Arg     Asn     Met     Lys     Val     Met     Leu     Ser     Ile
        80                              85                                      90

Gly     Gly     Trp     Thr     Trp     Ser     Thr     Asn     Phe     Pro     Ala     Ala     Ala     Ser     Ser     Ala
95                              100                                     105                                             110

Ala     Thr     Arg     Lys     Thr     Phe     Ala     Gln     Ser     Ala     Val     Gly     Phe     Met     Lys     Asp
                        115                                     120                                     125

Trp     Gly     Phe     Asp     Gly     Ile     Asp     Ile     Asp     Trp     Glu     Tyr     Pro     Ala     Asp     Ala
                        130                             135                                     140

Thr     Gln     Ala     Gln     Asn     Met     Val     Leu     Leu     Leu     Gln     Ala     Val     Arg     Ser     Glu
                        145                             150                                     155

Leu     Asp     Ser     Tyr     Ala     Ala     Gln     Tyr     Ala     Lys     Gly     His     His     Phe     Leu     Leu
        160                             165                                     170

Ser     Ile     Ala     Ala     Pro     Ala     Gly     Pro     Asp     Asn     Tyr     Asn     Lys     Leu     Lys     Phe
175                             180                                     185                                             190

Ala     Glu     Leu     Gly     Lys     Val     Leu     Asp     Tyr     Ile     Asn     Leu     Met     Ala     Tyr     Asp
                        195                             200                                     205

Tyr     Ala     Gly     Ser     Trp     Ser     Asn     Tyr     Thr     Gly     His     Asp     Ala     Asn     Ile     Tyr
                        210                             215                                     220

Ala     Asn     Pro     Gln     Asn     Pro     Asn     Ala     Thr     Pro     Tyr     Asn     Thr     Asp     Asp     Ala
                225                             230                                     235

Val     Gln     Ala     Tyr     Ile     Asn     Gly     Gly     Val     Pro     Ala     Asn     Lys     Ile     Val     Leu
        240                             245                                     250

Gly     Met     Pro     Ile     Tyr     Gly     Arg     Ser     Phe     Gln     Gln     Thr     Glu     Gly     Ile     Gly
255                             260                                     265                                             270

Lys     Pro     Tyr     Asn     Gly     Ile     Gly     Ser     Gly     Ser     Trp     Glu     Asn     Gly     Ile     Trp
                        275                             280                                             285

Asp     Tyr     Lys     Ala     Leu     Pro     Lys     Ala     Gly     Ala     Thr     Val     Lys     Cys     Asp     Asp
                        290                             295                                     300

Thr     Ala     Lys     Gly     Cys     Tyr     Ser     Tyr     Asp     Pro     Ser     Thr     Lys     Glu     Leu     Ile
                305                             310                                     315

Ser     Phe     Asp     Thr     Pro     Ala     Met     Ile     Ser     Thr     Lys     Val     Ser     Trp     Leu     Lys
        320                             325                                     330

Gly     Lys     Gly     Leu     Gly     Gly     Ser     Met     Phe     Trp     Glu     Ala     Ser     Ala     Asp     Lys
335                             340                                     345                                             350

Lys     Gly     Ser     Asp     Ser     Leu     Ile     Ser     Thr     Ser     His     Gln     Gly     Leu     Gly     Ser
```

355                          360                                  365
Gln Asp Ser Thr Gln Asn Tyr Leu Asp Tyr Pro Asn Ser Lys Tyr Asp
            370                      375                          380

Asn Ile Lys Lys Gly Met Asn
        385

( 2 ) INFORMATION FOR SEQ ID NO:11:

( i ) SEQUENCE CHARACTERISTICS:
        ( A ) LENGTH: 1701 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 266..320
        ( D ) OTHER INFORMATION: /number=1

( i x ) FEATURE:
        ( A ) NAME/KEY: intron
        ( B ) LOCATION: 420..472
        ( D ) OTHER INFORMATION: /number=2

( i x ) FEATURE:
        ( A ) NAME/KEY: intron
        ( B ) LOCATION: 523..571
        ( D ) OTHER INFORMATION: /number=3

( i x ) FEATURE:
        ( A ) NAME/KEY: CDS
        ( B ) LOCATION: join(126..265, 321..419, 473..522, 572..1551)

( i x ) FEATURE:
        ( A ) NAME/KEY: sigpeptide
        ( B ) LOCATION: 126..227

( i x ) FEATURE:
        ( A ) NAME/KEY: matpeptide
        ( B ) LOCATION: join(228..265, 321..419, 473..522, 572..1551)

( x i ) SEQUENCE DESCRIPTION: SEQ ID NO:11:

```
TCGGCCTCTC TCAACTCTTC TCTATCAGCA GCAACTCAAT AGGTACAAGC CTAACAGCAT          60

AGCTCCCTCT AGAGTCAGCA CGCCGAATCA GTTGATTCTC TACAACCTTC TGTACCTCAA         120

CTACT ATG TTG AGC TTT GTC AAA AAG TCG ATC GCC TTG GTG GCG GCC             167
      Met Leu Ser Phe Val Lys Lys Ser Ile Ala Leu Val Ala Ala
      -34          -30                 -25

CTG CAG GCG GTC ACT GCC CTG GCC ACG CCA ATC TCC AGT GAA GCT GGT           215
Leu Gln Ala Val Thr Ala Leu Ala Thr Pro Ile Ser Ser Glu Ala Gly
-20              -15                 -10                     - 5

GTT GAG AAG CGC GGT AGT GGT TTT GCA AAT GCC GTC TAC TTC ACC AAC TG        265
Val Glu Lys Arg Gly Ser Gly Phe Ala Asn Ala Val Tyr Phe Thr Asn Trp
                1               5                   10

GTTTGTGCAT CCTCATCTTG TTATCTCTTG TTCGTAATAG TTAACGAATG TTTAG G            321

GGC ATT TAT GGC CGC AAC TTC CAG CCT GCC GAC CTT CCT GCC TCG GAG           369
Gly Ile Tyr Gly Arg Asn Phe Gln Pro Ala Asp Leu Pro Ala Ser Glu
        15                  20                  25

ATT ACT CAC GTA CTC TAC TCC TTC ATG AAT GTC CGC GCA GAT GGC ACC AT        419
Ile Thr His Val Leu Tyr Ser Phe Met Asn Val Arg Ala Asp Gly Thr Ile
30                  35                  40                  45

GTGAGTGATG GAGTTCCTAG ATCTTGTGCC GCATTTCTG ACAAAGCAAC TAG C TTT           476
                                                            Phe

TCC GGT GAT ACC TAT GCC GAC TAC GAG AAG CAC TAC GCT GGT GAC T             522
Ser Gly Asp Thr Tyr Ala Asp Tyr Glu Lys His Tyr Ala Gly Asp
        50                  55                  60

GTGAGAATCT CTACATTTCT TTTGGCAAAA AGAAGAAACT AACAATTAG CT TGG              576
```

|  |  |  |  |  |  |  |  |  |  |  |  |  |  |  | Ser | Trp |  |
|---|---|---|---|---|---|---|---|---|---|---|---|---|---|---|---|---|---|

```
AAC  GAT  GTG  GGC  ACG  AAC  GCT  TAC  GGT  TGT  GTT  AAG  CAA  CTT  TAT  CTT        624
Asn  Asp  Val  Gly  Thr  Asn  Ala  Tyr  Gly  Cys  Val  Lys  Gln  Leu  Tyr  Leu
 65                       70                       75                        80

CTC  AAG  AAG  CAG  AAC  CGC  AAC  ATG  AAG  GTG  ATG  CTG  TCG  ATT  GGT  GGT        672
Leu  Lys  Lys  Gln  Asn  Arg  Asn  Met  Lys  Val  Met  Leu  Ser  Ile  Gly  Gly
                          85                       90                        95

TGG  ACA  TGG  TCT  ACC  AAC  TTC  CCC  GCT  GCC  GCC  AGC  TCG  GCT  GCT  ACC        720
Trp  Thr  Trp  Ser  Thr  Asn  Phe  Pro  Ala  Ala  Ala  Ser  Ser  Ala  Ala  Thr
                     100                      105                      110

CGA  AAG  ACT  TTT  GCT  CAG  TCT  GCT  GTT  GGC  TTC  ATG  AAG  GAC  TGG  GGT        768
Arg  Lys  Thr  Phe  Ala  Gln  Ser  Ala  Val  Gly  Phe  Met  Lys  Asp  Trp  Gly
           115                      120                      125

TTC  GAC  GGT  ATT  GAT  ATC  GAC  TGG  GAG  TAC  CCC  GCC  GAT  GCC  ACT  CAG        816
Phe  Asp  Gly  Ile  Asp  Ile  Asp  Trp  Glu  Tyr  Pro  Ala  Asp  Ala  Thr  Gln
      130                      135                      140

GCT  CAG  AAT  ATG  GTT  CTC  TTG  CTA  CAG  GCT  GTC  CGC  AGT  GAG  CTC  GAC        864
Ala  Gln  Asn  Met  Val  Leu  Leu  Leu  Gln  Ala  Val  Arg  Ser  Glu  Leu  Asp
 145                      150                      155                      160

TCC  TAC  GCT  GCC  CAG  TAC  GCC  AAG  GGT  CAC  CAC  TTC  CTG  CTT  TCA  ATT        912
Ser  Tyr  Ala  Ala  Gln  Tyr  Ala  Lys  Gly  His  His  Phe  Leu  Leu  Ser  Ile
                     165                      170                      175

GCC  GCC  CCT  GCT  GGA  CCT  GAC  AAT  TAT  AAC  AAG  CTG  AAG  TTT  GCT  GAG        960
Ala  Ala  Pro  Ala  Gly  Pro  Asp  Asn  Tyr  Asn  Lys  Leu  Lys  Phe  Ala  Glu
                180                      185                      190

CTT  GGC  AAG  GTT  CTC  GAT  TAC  ATT  AAC  CTC  ATG  GCT  TAC  GAT  TAC  GCT       1008
Leu  Gly  Lys  Val  Leu  Asp  Tyr  Ile  Asn  Leu  Met  Ala  Tyr  Asp  Tyr  Ala
           195                      200                      205

GGA  TCT  TGG  AGC  AAC  TAC  ACT  GGC  CAC  GAT  GCC  AAC  ATA  TAC  GCA  AAC       1056
Gly  Ser  Trp  Ser  Asn  Tyr  Thr  Gly  His  Asp  Ala  Asn  Ile  Tyr  Ala  Asn
      210                      215                      220

CCG  CAG  AAC  CCC  AAC  GCC  ACC  CCT  TAC  AAC  ACG  GAC  GAT  GCT  GTC  CAG       1104
Pro  Gln  Asn  Pro  Asn  Ala  Thr  Pro  Tyr  Asn  Thr  Asp  Asp  Ala  Val  Gln
 225                      230                      235                      240

GCC  TAT  ATC  AAC  GGC  GGC  GTC  CCT  GCC  AAC  AAG  ATC  GTC  CTT  GGT  ATG       1152
Ala  Tyr  Ile  Asn  Gly  Gly  Val  Pro  Ala  Asn  Lys  Ile  Val  Leu  Gly  Met
                     245                      250                      255

CCA  ATC  TAC  GGC  CGA  TCC  TTC  CAG  CAA  ACC  GAG  GGT  ATC  GGT  AAG  CCT       1200
Pro  Ile  Tyr  Gly  Arg  Ser  Phe  Gln  Gln  Thr  Glu  Gly  Ile  Gly  Lys  Pro
                260                      265                      270

TAC  AAT  GGT  ATT  GGC  TCT  GGT  AGC  TGG  GAG  AAC  GGT  ATC  TGG  GAC  TAC       1248
Tyr  Asn  Gly  Ile  Gly  Ser  Gly  Ser  Trp  Glu  Asn  Gly  Ile  Trp  Asp  Tyr
           275                      280                      285

AAG  GCT  CTC  CCC  AAG  GCT  GGT  GCC  ACC  GTC  AAG  TGC  GAC  GAT  ACC  GCC       1296
Lys  Ala  Leu  Pro  Lys  Ala  Gly  Ala  Thr  Val  Lys  Cys  Asp  Asp  Thr  Ala
 290                      295                      300

AAG  GGA  TGC  TAC  AGC  TAC  GAT  CCA  AGC  ACT  AAG  GAG  CTT  ATT  TCT  TTC       1344
Lys  Gly  Cys  Tyr  Ser  Tyr  Asp  Pro  Ser  Thr  Lys  Glu  Leu  Ile  Ser  Phe
 305                      310                      315                      320

GAT  ACG  CCG  GCT  ATG  ATC  AGC  ACC  AAA  GTT  AGC  TGG  CTC  AAG  GGC  AAG       1392
Asp  Thr  Pro  Ala  Met  Ile  Ser  Thr  Lys  Val  Ser  Trp  Leu  Lys  Gly  Lys
                     325                      330                      335

GGC  CTT  GGC  GGC  AGC  ATG  TTC  TGG  GAG  GCT  TCT  GCC  GAC  AAG  AAG  GGC       1440
Gly  Leu  Gly  Gly  Ser  Met  Phe  Trp  Glu  Ala  Ser  Ala  Asp  Lys  Lys  Gly
                340                      345                      350

TCG  GAC  TCT  CTT  ATT  AGC  ACC  AGC  CAC  CAA  GGT  CTC  GGT  AGC  CAG  GAC       1488
Ser  Asp  Ser  Leu  Ile  Ser  Thr  Ser  His  Gln  Gly  Leu  Gly  Ser  Gln  Asp
           355                      360                      365

AGC  ACT  CAG  AAC  TAC  CTC  GAC  TAC  CCT  AAC  TCC  AAG  TAC  GAC  AAC  ATC       1536
Ser  Thr  Gln  Asn  Tyr  Leu  Asp  Tyr  Pro  Asn  Ser  Lys  Tyr  Asp  Asn  Ile
 370                      375                      380
```

-continued

```
AAG  AAG  GGC  ATG  AAC  TAAGCAGTCG GTGTTTGCAT AGCTTGATTG ATGCTCGAGG        1591
Lys  Lys  Gly  Met  Asn
385

TTGGATGTGG TCCGCGCTGT ATATATTTCC AAACCAGCCT TACCCTGAGG CTTATCAAGT           1651

CATTCTATAC TTTCAACGTA CATATTATTG CTGCCATTGG CATGCAAATA                     1701
```

(2) INFORMATION FOR SEQ ID NO:12:

(i) SEQUENCE CHARACTERISTICS:
        (A) LENGTH: 423 amino acids
        (B) TYPE: amino acid
        (D) TOPOLOGY: linear (ii) MOLECULE TYPE: protein (xi) SEQUENCE DESCRIPTION: SEQ ID NO:12:

```
Met  Leu  Ser  Phe  Val  Lys  Lys  Ser  Ile  Ala  Leu  Val  Ala  Ala  Leu  Gln
-34            -30                 -25                           -20

Ala  Val  Thr  Ala  Leu  Ala  Thr  Pro  Ile  Ser  Ser  Glu  Ala  Gly  Val  Glu
               -15                      -10                      -5

Lys  Arg  Gly  Ser  Gly  Phe  Ala  Asn  Ala  Val  Tyr  Phe  Thr  Asn  Trp  Gly
          1                   5                        10

Ile  Tyr  Gly  Arg  Asn  Phe  Gln  Pro  Ala  Asp  Leu  Pro  Ala  Ser  Glu  Ile
15                  20                       25                           30

Thr  His  Val  Leu  Tyr  Ser  Phe  Met  Asn  Val  Arg  Ala  Asp  Gly  Thr  Ile
               35                      40                           45

Phe  Ser  Gly  Asp  Thr  Tyr  Ala  Asp  Tyr  Glu  Lys  His  Tyr  Ala  Gly  Asp
               50                      55                           60

Ser  Trp  Asn  Asp  Val  Gly  Thr  Asn  Ala  Tyr  Gly  Cys  Val  Lys  Gln  Leu
               65                      70                           75

Tyr  Leu  Leu  Lys  Lys  Gln  Asn  Arg  Asn  Met  Lys  Val  Met  Leu  Ser  Ile
          80                       85                      90

Gly  Gly  Trp  Thr  Trp  Ser  Thr  Asn  Phe  Pro  Ala  Ala  Ala  Ser  Ser  Ala
95                       100                      105                      110

Ala  Thr  Arg  Lys  Thr  Phe  Ala  Gln  Ser  Ala  Val  Gly  Phe  Met  Lys  Asp
               115                      120                           125

Trp  Gly  Phe  Asp  Gly  Ile  Asp  Ile  Asp  Trp  Glu  Tyr  Pro  Ala  Asp  Ala
               130                      135                           140

Thr  Gln  Ala  Gln  Asn  Met  Val  Leu  Leu  Leu  Gln  Ala  Val  Arg  Ser  Glu
               145                      150                           155

Leu  Asp  Ser  Tyr  Ala  Ala  Gln  Tyr  Ala  Lys  Gly  His  His  Phe  Leu  Leu
     160                      165                      170

Ser  Ile  Ala  Ala  Pro  Ala  Gly  Pro  Asp  Asn  Tyr  Asn  Lys  Leu  Lys  Phe
175                      180                      185                      190

Ala  Glu  Leu  Gly  Lys  Val  Leu  Asp  Tyr  Ile  Asn  Leu  Met  Ala  Tyr  Asp
               195                      200                           205

Tyr  Ala  Gly  Ser  Trp  Ser  Asn  Tyr  Thr  Gly  His  Asp  Ala  Asn  Ile  Tyr
               210                      215                           220

Ala  Asn  Pro  Gln  Asn  Pro  Asn  Ala  Thr  Pro  Tyr  Asn  Thr  Asp  Asp  Ala
          225                      230                      235

Val  Gln  Ala  Tyr  Ile  Asn  Gly  Gly  Val  Pro  Ala  Asn  Lys  Ile  Val  Leu
240                      245                      250

Gly  Met  Pro  Ile  Tyr  Gly  Arg  Ser  Phe  Gln  Gln  Thr  Glu  Gly  Ile  Gly
255                      260                      265                      270

Lys  Pro  Tyr  Asn  Gly  Ile  Gly  Ser  Gly  Ser  Trp  Glu  Asn  Gly  Ile  Trp
               275                      280                           285

Asp  Tyr  Lys  Ala  Leu  Pro  Lys  Ala  Gly  Ala  Thr  Val  Lys  Cys  Asp  Asp
               290                      295                           300
```

| | | | | | | | | | | | | | |
|---|---|---|---|---|---|---|---|---|---|---|---|---|---|
|Thr|Ala|Lys<br>305|Gly|Cys|Tyr|Ser|Tyr<br>310|Asp|Pro|Ser|Thr|Lys<br>315|Glu|Leu|Ile|
|Ser|Phe<br>320|Asp|Thr|Pro|Ala|Met<br>325|Ile|Ser|Thr|Lys|Val<br>330|Ser|Trp|Leu|Lys|
|Gly<br>335|Lys|Gly|Leu|Gly|Gly<br>340|Ser|Met|Phe|Trp|Glu<br>345|Ala|Ser|Ala|Asp|Lys<br>350|
|Lys|Gly|Ser|Asp|Ser<br>355|Leu|Ile|Ser|Thr|Ser<br>360|His|Gln|Gly|Leu|Gly<br>365|Ser|
|Gln|Asp|Ser|Thr<br>370|Gln|Asn|Tyr|Leu|Asp<br>375|Tyr|Pro|Asn|Ser|Lys<br>380|Tyr|Asp|
|Asn|Ile|Lys<br>385|Lys|Gly|Met|Asn| | | | | | | | | |

(2) INFORMATION FOR SEQ ID NO:13:

(i) SEQUENCE CHARACTERISTICS:
        (A) LENGTH: 1364 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
GGATCCGCTA ACTGACATCG ATATACACAA TGTTGAGCTT TGTCAAAAAG TCGATCGCCT      60
TGGTGGCGGC CCTGCAGGCG GTCACTGCCC TGGCCACGCC AATCTCCAGT GAAGCTGGTG     120
TTGAGAAGCG CGGTAGTGGT TTTGCAAATG CCGTCTACTT CACCAACTGG GGCATTTATG     180
GCCGCAACTT CCAGCCTGCC GACCTTCCTG CCTCGGAGAT TACTCACGTA CTCTACTCCT     240
TCATGAATGT CCGCGCAGAT GGCACCATCT TTTCCGGTGA TACCTATGCC GACTACGAGA     300
AGCACTACGC TGGTGACTCT TGGAACGATG TGGGCACGAA CGCTTACGGT TGTGTTAAGC     360
AACTTTATCT TCTCAAGAAG CAGAACCGCA ACATGAAGGT GATGCTGTCG ATTGGTGGTT     420
GGACATGGTC TACCAACTTC CCCGCTGCCG CCAGCTCGGC TGCTACCCGA AAGACTTTTG     480
CTCAGTCTGC TGTTGGCTTC ATGAAGGACT GGGGTTTCGA CGGTATTGAT ATCGACTGGG     540
AGTACCCCGC CGATGCCACT CAGGCTCAGA ATATGGTTCT CTTGCTACAG GCTGTCCGCA     600
GTGAGCTCGA CTCCTACGCT GCCCAGTACG CCAAGGGTCA CCACTTCCTG CTTTCAATTG     660
CCGCCCCTGC TGGACCTGAC AATTATAACA AGCTGAAGTT TGCTGAGCTT GGCAAGGTTC     720
TCGATTACAT TAACCTCATG GCTTACGATT ACGCTGGATC TTGGAGCAAC TACACTGGCC     780
ACGATGCCAA CATATACGCA AACCCGCAGA ACCCCAACGC CACCCCTTAC AACACGGACG     840
ATGCTGTCCA GGCCTATATC AACGGCGGCG TCCCTGCCAA CAAGATCGTC CTTGGTATGC     900
CAATCTACGG CCGATCCTTC AGCAAACCG AGGGTATCGG TAAGCCTTAC AATGGTATTG     960
GCTCTGGTAG CTGGGAGAAC GGTATCTGGG ACTACAAGGC TCTCCCCAAG GCTGGTGCCA    1020
CCGTCAAGTG CGACGATACC GCCAAGGGAT GCTACAGCTA CGATCCAAGC ACTAAGGAGC    1080
TTATTTCTTT CGATACGCCG GCTATGATCA GCACCAAAGT TAGCTGGCTC AAGGGCAAGG    1140
GCCTTGGCGG CAGCATGTTC TGGGAGGCTT CTGCCGACAA GAAGGGCTCG GACTCTCTTA    1200
TTAGCACCAG CCACCAAGGT CTCGGTAGCC AGGACAGCAC TCAGAACTAC CTCGACTACC    1260
CTAACTCCAA GTACGACAAC ATCAAGAAGG GCATGAACTA AGCAGTCGGT GTTTGCATAG    1320
CTTGATTGAT GCTCGACTCT AGAGGATCGA ACTGTACCGA GCTC                     1364
```

(2) INFORMATION FOR SEQ ID NO:14:

(i) SEQUENCE CHARACTERISTICS:

(A) LENGTH: 1320 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:14:

| | | | | | | | |
|---|---|---|---|---|---|---|---|
| GGATCCATGA | AGAAGAATAG | GATGATGATG | ATGATATGGA | GCGTAGGAGT | GGTGTGGATG | | 60 |
| CTGTTGTTGG | TTGGAGGAAG | CTACGGAGGT | AGTGGTTTTG | CAAATGCCGT | CTACTTCACC | | 120 |
| AACTGGGGCA | TTTATGGCCG | CAACTTCCAG | CCTGCCGACC | TTCCTGCCTC | GGAGATTACT | | 180 |
| CACGTACTCT | ACTCCTTCAT | GAATGTCCGC | GCAGATGGCA | CCATCTTTTC | CGGTGATACC | | 240 |
| TATGCCGACT | ACGAGAAGCA | CTACGCTGGT | GACTCTTGGA | ACGATGTGGG | CACGAACGCT | | 300 |
| TACGGTTGTG | TTAAGCAACT | TTATCTTCTC | AAGAAGCAGA | ACCGCAACAT | GAAGGTGATG | | 360 |
| CTGTCGATTG | GTGGTTGGAC | ATGGTCTACC | AACTTCCCCG | CTGCCGCCAG | CTCGGCTGCT | | 420 |
| ACCCGAAAGA | CTTTTGCTCA | GTCTGCTGTT | GGCTTCATGA | GGACTGGGG | TTTCGACGGT | | 480 |
| ATTGATATCG | ACTGGGAGTA | CCCCGCCGAT | GCCACTCAGG | CTCAGAATAT | GGTTCTCTTG | | 540 |
| CTACAGGCTG | TCCGCAGTGA | GCTCGACTCC | TACGCTGCCC | AGTACGCCAA | GGGTCACCAC | | 600 |
| TTCCTGCTTT | CAATTGCCGC | CCCTGCTGGA | CCTGACAATT | ATAACAAGCT | GAAGTTTGCT | | 660 |
| GAGCTTGGCA | AGGTTCTCGA | TTACATTAAC | CTCATGGCTT | ACGATTACGC | TGGATCTTGG | | 720 |
| AGCAACTACA | CTGGCCACGA | TGCCAACATA | TACGCAAACC | CGCAGAACCC | CAACGCCACC | | 780 |
| CCTTACAACA | CGGACGATGC | TGTCCAGGCC | TATATCAACG | GCGGCGTCCC | TGCCAACAAG | | 840 |
| ATCGTCCTTG | GTATGCCAAT | CTACGGCCGA | TCCTTCCAGC | AAACCGAGGG | TATCGGTAAG | | 900 |
| CCTTACAATG | GTATTGGCTC | TGGTAGCTGG | GAGAACGGTA | TCTGGGACTA | CAAGGCTCTC | | 960 |
| CCCAAGGCTG | GTGCCACCGT | CAAGTGCGAC | GATACCGCCA | AGGGATGCTA | CAGCTACGAT | | 1020 |
| CCAAGCACTA | AGGAGCTTAT | TTCTTTCGAT | ACGCCGGCTA | TGATCAGCAC | CAAAGTTAGC | | 1080 |
| TGGCTCAAGG | GCAAGGGCCT | TGGCGGCAGC | ATGTTCTGGG | AGGCTTCTGC | CGACAAGAAG | | 1140 |
| GGCTCGGACT | CTCTTATTAG | CACCAGCCAC | CAAGGTCTCG | GTAGCCAGGA | CAGCACTCAG | | 1200 |
| AACTACCTCG | ACTACCCTAA | CTCCAAGTAC | GACAACATCA | AGAAGGGCAT | GAACTAAGCA | | 1260 |
| GTCGGTGTTT | GCATAGCTTG | ATTGATGCTC | GACTCTAGAG | GATCGAACTG | TACCGAGCTC | | 1320 |

(2) INFORMATION FOR SEQ ID NO:15:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: miscfeature
(B) LOCATION: 3
(D) OTHER INFORMATION: /note="N =inosine"

(ix) FEATURE:
(A) NAME/KEY: miscfeature
(B) LOCATION: 9
(D) OTHER INFORMATION: /note="N =inosine"

(ix) FEATURE:
(A) NAME/KEY: miscfeature
(B) LOCATION: 15
(D) OTHER INFORMATION: /note="N =inosine"

(ix) FEATURE:
(A) NAME/KEY: miscfeature
(B) LOCATION: 18

( D ) OTHER INFORMATION: /note="N =inosine"

( x i ) SEQUENCE DESCRIPTION: SEQ ID NO:15:

GGNTTYGCNA AYGCNGTNTA YTTYAC 26

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

Gly Phe Ala Asn Ala Val Tyr Phe
1               5

( 2 ) INFORMATION FOR SEQ ID NO:17:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GATCCGGGCC CT 12

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CAAATGCCGT CTACTTCACC 20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

CCTCATGGCT TACGATTACG 20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

TCCAACCTCG AGCATCAATC 20

( 2 ) INFORMATION FOR SEQ ID NO:21:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

Met Leu Ser Phe Val Lys Lys Ser Ile Ala Leu Val Ala Ala Leu Gln
 1               5                  10                    15

Ala Val Thr Ala Leu Ala Thr Pro Ile Ser Ser Glu Ala Gly Val Glu
             20                  25                30

Lys Arg ( 2 ) INFORMATION FOR SEQ ID NO:22:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:22:

TATGGGTAGT GGTTTTGCAA ATGCCGT                                27

( 2 ) INFORMATION FOR SEQ ID NO:23:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:23:

AGCTTGGATA AAAGAGGTAG TGGTTTTGCA AATGCCGT                    38

( 2 ) INFORMATION FOR SEQ ID NO:24:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:24:

CGATATACAC AATGTTGAGC TTTGTCAAAA AGTCGATCGC CTTGGTGGCG GCCCTGCA   58

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:25:

GATCCGCTAA CTGACAT                                           17

( 2 ) INFORMATION FOR SEQ ID NO:26:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:26:

GATCGAACTG TACCGAGCT                                               19

( 2 ) INFORMATION FOR SEQ ID NO:27:

( i ) SEQUENCE CHARACTERISTICS:
    ( A ) LENGTH: 109 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:27:

GATCCATGAA GAAGAATAGG ATGATGATGA TGATATGGAG CGTAGGAGTG GTGTGGATGC   60

TGTTGTTGGT TGGAGGAAGC TACGGAGGTA GTGGTTTTGC AAATGCCGT              109

( 2 ) INFORMATION FOR SEQ ID NO:28:

( i ) SEQUENCE CHARACTERISTICS:
    ( A ) LENGTH: 27 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:28:

Met Lys Lys Asn Arg Met Met Met Ile Trp Ser Val Gly Val Val
1               5                   10                  15

Trp Met Leu Leu Leu Val Gly Gly Ser Tyr Gly
            20                  25

( 2 ) INFORMATION FOR SEQ ID NO:29:

( i ) SEQUENCE CHARACTERISTICS:
    ( A ) LENGTH: 81 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( B ) CLONE: sequence coding for SEQ ID NO: 28

( x i ) SEQUENCE DESCRIPTION: SEQ ID NO:29:

ATGAAGAAGA ATAGGATGAT GATGATGATA TGGAGCGTAG GAGTGGTGTG GATGCTGTTG   60

TTGGTTGGAG GAAGCTACGG A                                            81

What is claimed is:

1. A recombinant DNA construct which codes for a protein with endochitinase activity, wherein said protein comprises the following sequence (a1) (SEQ ID NO:1):

Gly Ser Gly Phe Ala Asn Ala Val Tyr Phe Thr Asn Trp Gly Ile
1               5                   10                  15

Tyr Gly Arg Asn Phe Gln Pro Ala Asp Leu Pro Ala Ser Glu Ile
            20                  25                  30

Thr His Val Leu Tyr Ser Phe Met Asn Val Arg Ala Asp Gly Thr
            35                  40                  45

Ile Phe Ser Gly Asp Thr Tyr Ala Asp Tyr Glu Lys His Tyr Ala
            50                  55                  60

Gly Asp Ser Trp Asn Asp Val Gly Thr Asn Ala Tyr Gly Cys Val
            65                  70                  75

Lys Gln Leu Tyr Leu Leu Lys Lys Gln Asn Arg Asn Met Lys Val
            80                  85                  90

-continued

Met Leu Ser Ile Gly Gly Trp Thr Trp Ser Thr Asn Phe Pro Ala
            95                    100                   105

Ala Ala Ser Ser Ala Ala Thr Arg Lys Thr Phe Ala Gln Ser Ala
            110                   115                   120

Val Gly Phe Met Lys Asp Trp Gly Phe Asp Gly Ile Asp Ile Asp
            125                   130                   135

Trp Glu Tyr Pro Ala Asp Ala Thr Gln Ala Gln Asn Met Val Leu
            140                   145                   150

Leu Leu Gln Ala Val Arg Ser Glu Leu Asp Ser Tyr Ala Ala Gln
            155                   160                   165

Tyr Ala Lys Gly His His Phe Leu Leu Ser Ile Ala Ala Pro Ala
            170                   175                   180

Gly Pro Asp Asn Tyr Asn Lys Leu Lys Phe Ala Glu Leu Gly Lys
            185                   190                   195

Val Leu Asp Tyr Ile Asn Leu Met Ala Tyr Asp Tyr Ala Gly Ser
            200                   205                   210

Trp Ser Asn Tyr Thr Gly His Asp Ala Asn Ile Tyr Ala Asn Pro
            215                   220                   225

Gln Asn Pro Asn Ala Thr Pro Tyr Asn Thr Asp Asp Ala Val Gln
            230                   235                   240

Ala Tyr Ile Asn Gly Gly Val Pro Ala Asn Lys Ile Val Leu Gly
            245                   250                   255

Met Pro Ile Tyr Gly Arg Ser Phe Gln Gln Thr Glu Gly Ile Gly
            260                   265                   270

Lys Pro Tyr Asn Gly Ile Gly Ser Gly Ser Trp Glu Asn Gly Ile
            275                   280                   285

Trp Asp Tyr Lys Ala Leu Pro Lys Ala Gly Ala Thr Val Lys Cys
            290                   295                   300

Asp Asp Thr Ala Lys Gly Cys Tyr Ser Tyr Asp PRo Ser Thr Lys
            305                   310                   315

Glu Leu Ile Ser Phe Asp Thr Pro Ala Met Ile Ser Thr Lys Val
            320                   325                   330

-continued

Ser Trp Leu Lys Gly Lys Gly Leu Gly Gly Ser Met Phe Trp Glu
            335                   340                   345

Ala Ser Ala Asp Lys Lys Gly Ser Asp Ser Leu Ile Ser Thr Ser
            350                   355                   360

His Gln gly Leu Gly Ser Gln Asp Ser Thr Gln Asn Tyr Leu Asp
            365                   370                   375

Tyr Pro Asn Ser Lys Tyr Asp Asn Ile Lys Gly Met Asn.
            380                   385

2. A recombinant DNA construct according to claim 1 which contains a signal sequence upstream of the sequence (a1).

3. A recombinant DNA construct according to claim 2 wherein the signal sequence is a sequence coding for the signal peptide of the following sequence (a2)(SEQ ID NO:4):

Met Leu Ser Phe Val Lys Lys Ser Ile Ala Leu Val Ala Ala Leu Gln
1               5                   10                  15
Ala Val Thr Ala Leu Ala.
            20

4. A recombinant DNA construct according to claim 2 wherein the signal peptide coded by the signal sequence is separated from the sequence (a1) of the coded protein by the peptide of the following sequence (a3)-(SEQ ID NO:5):

Thr Pro Ile Ser Ser Glu Ala Gly Val Glu Lys Arg.
1               5                       10

5. A recombinant DNA construct according to claim 2 wherein the signal sequence is a sequence coding for the signal peptide of the following sequence (a5)(SEQ ID NO:28):

Met Lys Lys Asn Arg Met Met Met Met Ile Trp Ser Val Gly Val Val
1               5                   10                  15
Trp Met Leu Leu Leu Val Gly Gly Ser Tyr Gly.
            20                  25

6. A recombinant DNA construct according claim 1 which comprises a promoter sequence containing the 35S promoter of cauliflower mosaic virus.

7. A recombinant DNA construct according to claim 1 which comprises a terminator sequence containing the transcription termination sequence of the nopaline synthase gene of *Agrobacterium tumefaciens*.

8. A recombinant DNA construct according to claim 1 wherein the nucleotide sequence coding for the amino acid sequence (a1) is the following sequence (Na1)(SEQ ID NO:6):

```
GGTAGTGGTT TTGCAAATGC CGTCTACTTC ACCAACTGGG GCATTTATGG CCGCAACTTC    60
CAGCCTGCCG ACCTTCCTGC CTCGGAGATT ACTCACGTAC TCTACTCCTT CATGAATGTC   120
CGCGCAGATG GCACCATCTT TTCCGGTGAT ACCTATGCCG ACTACGAGAA GCACTACGCT   180
GGTGACTCTT GGAACGATGT GGGCACGAAC GCTTACGGTT GTGTTAAGCA ACTTTATCTT   240
CTCAAGAAGC AGAACCGCAA CATGAAGGTG ATGCTGTCGA TTGGTGGTTG GACATGGTCT   300
ACCAACTTCC CCGCTGCCGC CAGCTCGGCT GCTACCCGAA AGACTTTTGC TCAGTCTGCT   360
GTTGGCTTCA TGAAGGACTG GGGTTTCGAC GGTATTGATA TCGACTGGGA GTACCCCGCC   420
GATGCCACTC AGGCTCAGAA TATGGTTCTC TTGCTACAGG CTGTCCGCAG TGAGCTCGAC   480
TCCTACGCTG CCCAGTACGC CAAGGGTCAC CACTTCCTGC TTTCAATTGC CGCCCCTGCT   540
GGACCTGACA ATTATAACAA GCTGAAGTTT GCTGAGCTTG GCAAGGTTCT CGATTACATT   600
AACCTCATGG CTTACGATTA CGCTGGATCT TGGAGCAACT ACACTGGCCA CGATGCCAAC   660
ATATACGCAA ACCCGCAGAA CCCCAACGCC ACCCCTTACA ACACGGACGA TGCTGTCCAG   720
GCCTATATCA ACGGCGGCGT CCCTGCCAAC AAGATCGTCC TTGGTATGCC AATCTACGGC   780
CGATCCTTCC AGCAAACCGA GGGTATCGGT AAGCCTTACA ATGGTATTGG CTCTGGTAGC   840
TGGGAGAACG GTATCTGGGA CTACAAGGCT CTCCCCAAGG CTGGTGCCAC CGTCAAGTGC   900
GACGATACCG CCAAGGGATG CTACAGCTAC GATCCAAGCA CTAAGGAGCT TATTTCTTTC   960
```

```
GATACGCCGG CTATGATCAG CACCAAAGTT AGCTGGCTCA AGGGCAAGGG CCTTGGCGGC  1020
AGCATGTTCT GGGAGGCTTC TGCCGACAAG AAGGGCTCGG ACTCTCTTAT TAGCACCAGC  1080
CACCAAGGTC TCGGTAGCCA GGACAGCACT CAGAACTACC TCGACTACCC TAACTCCAAG  1140
TACGACAACA TCAAGAAGGG CATGAAC                                      1167.
```

9. A recombinant DNA construct according to claim 3 wherein the nucleotide sequence coding for the amino acid sequence (a2) is the following sequence (Na2)(SEQ ID NO:7):

```
ATGTTGAGCT TTGTCAAAAA GTCGATCGCC TTGGTGGCGG CCCTGCAGGC GGTCACTGCC  60
CTGGCC                                                              66.
```

10. A recombinant DNA construct according to claim 4 wherein the nucleotide sequence coding for the amino acid sequence (a3) is the following sequence (Na3)(SEQ ID NO:8):

```
ACGCCAATCT CCAGTGAAGC TGGTGTTGAG AAGCGC  36.
```

11. A recombinant DNA construct according to claim 5 wherein the nucleotide sequence coding for the amino acid sequence (a5) is the following sequence (Na5)(SEQ ID NO:29):

```
ATGAAGAAGA ATAGGATGAT GATGATGATA TGGAGCGTAG GAGTGGTGTG GATGCTGTTG  60
TTGGTTGGAG GAAGCTACGG A                                             81.
```

12. A bacterium which contains the recombinant DNA construct according to claim 1, together with the means necessary for its replication and its expression.

13. A yeast which contains the recombinant DNA construct according to claim 1, together with the means necessary for its replication and its expression.

14. A filamentous fungus which contains the recombinant DNA construct according to claim 1, together with the means necessary for its replication and its expression.

15. A plant cell which is transformed by a recombinant DNA construct according to claim 1, together with the means necessary for its expression.

16. A plant cell according to claim 15, which belongs to one of the species of *Nicotiana tabacum, Helianthus annuus* and *Brassica napus*.

17. A recombinant DNA construct according to claim 3, wherein the signal peptide coded by the signal sequence is separated from the sequence (a1) of the coded protein by the peptide of the following sequence (a3) (SEQ ID NO:5):

Thr Pro Ile Ser Ser Glu Ala Gly Val Glu Lys Arg.
1         5                 10

* * * * *